United States Patent
Gliner et al.

(10) Patent No.: US 11,980,573 B2
(45) Date of Patent: May 14, 2024

(54) EYE EXAMINATION APPARATUS

(71) Applicant: JOHNSON & JOHNSON SURGICAL VISION, INC., Irvine, CA (US)

(72) Inventors: Vadim Gliner, Haifa (IL); Ilya Sitnitsky, Nahariya (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 790 days.

(21) Appl. No.: 16/704,054

(22) Filed: Dec. 5, 2019

(65) Prior Publication Data

US 2021/0169695 A1   Jun. 10, 2021

(51) Int. Cl.
| | |
|---|---|
| A61B 1/05 | (2006.01) |
| A61B 1/00 | (2006.01) |
| A61B 1/313 | (2006.01) |
| A61B 3/14 | (2006.01) |
| A61B 5/06 | (2006.01) |
| A61F 9/007 | (2006.01) |
| A61B 17/00 | (2006.01) |
| A61B 34/00 | (2016.01) |
| A61B 90/00 | (2016.01) |

(52) U.S. Cl.
CPC ...... *A61F 9/00745* (2013.01); *A61B 1/00045* (2013.01); *A61B 1/00087* (2013.01); *A61B 1/05* (2013.01); *A61B 1/313* (2013.01); *A61B 3/14* (2013.01); *A61B 5/062* (2013.01); *A61B 2017/00199* (2013.01); *A61B 34/76* (2016.02); *A61B 2090/374* (2016.02); *A61B 2090/376* (2016.02); *A61B 2090/3762* (2016.02); *A61B 2217/005* (2013.01); *A61B 2217/007* (2013.01)

(58) Field of Classification Search
CPC ... A61B 1/00045; A61B 1/00087; A61B 1/05; A61B 1/313; A61B 3/14; A61B 5/062; A61B 2017/00199; A61B 2217/005; A61F 9/00745

See application file for complete search history.

(56) References Cited

U.S. PATENT DOCUMENTS

| | | |
|---|---|---|
| 4,607,622 A | 8/1986 | Fritch et al. |
| 5,106,381 A | 4/1992 | Chikama |

(Continued)

FOREIGN PATENT DOCUMENTS

| | | |
|---|---|---|
| CN | 105640698 A | 6/2016 |
| EP | 0513224 B1 | 10/1996 |
| WO | 2020222238 A1 | 11/2020 |

OTHER PUBLICATIONS

Ajlan R.S., et al., "Endoscopic Vitreoretinal Surgery: Principles, Applications and New Directions," International Journal of Retina and Vitreous, Jun. 2019, 5 (15), 11 pages.

(Continued)

*Primary Examiner* — Anh Tuan T Nguyen
*Assistant Examiner* — Rynae E Boler
(74) *Attorney, Agent, or Firm* — Johnson & Johnson Surgical Vision, Inc.

(57) ABSTRACT

In one embodiment, an eye examination apparatus to inspect a vitreous humor of an eye, includes a probe including a shaft including a distal end, a camera disposed at the distal end, wherein the distal end and the camera are configured to be inserted into the vitreous humor, and a magnetic orientation sensor disposed at a section of the shaft.

20 Claims, 17 Drawing Sheets

(56) References Cited

U.S. PATENT DOCUMENTS

| | | | |
|---|---|---|---|
| 5,255,668 | A | 10/1993 | Umeda |
| 5,391,199 | A | 2/1995 | Ben-Haim |
| 5,443,489 | A | 8/1995 | Ben-Haim |
| 5,558,091 | A | 9/1996 | Acker et al. |
| 5,820,591 | A | 10/1998 | Thompson et al. |
| 5,855,560 | A | 1/1999 | Daomi et al. |
| 6,172,499 | B1 | 1/2001 | Ashe |
| 6,177,792 | B1 | 1/2001 | Govari et al. |
| 6,788,967 | B2 | 9/2004 | Ben-Haim et al. |
| 7,083,591 | B2 | 8/2006 | Cionni |
| 7,186,258 | B2 | 3/2007 | Sabet |
| 7,563,242 | B2 | 7/2009 | Yaguchi |
| 7,841,503 | B2 | 11/2010 | Sonnenschein et al. |
| 8,016,843 | B2 | 9/2011 | Escaf |
| 8,398,587 | B2 | 3/2013 | Dewaele et al. |
| 8,403,828 | B2 | 3/2013 | Mawn et al. |
| 8,708,488 | B2 | 4/2014 | Kraus |
| 9,364,982 | B2 | 6/2016 | Schaller |
| 9,463,081 | B2 | 10/2016 | Urakabe |
| 9,498,377 | B2 | 11/2016 | McCary |
| 9,962,226 | B2 | 5/2018 | Brennan |
| 10,524,822 | B2 | 1/2020 | Aljuri et al. |
| 10,561,822 | B2 | 2/2020 | Wang |
| 10,624,784 | B2 | 4/2020 | Saimovici |
| 2001/0010003 | A1 | 7/2001 | Lai |
| 2003/0191369 | A1 | 10/2003 | Arai et al. |
| 2005/0054900 | A1* | 3/2005 | Mawn ............... A61B 5/064 600/156 |
| 2005/0288627 | A1 | 12/2005 | Mogul |
| 2008/0058708 | A1 | 3/2008 | Akahoshi |
| 2009/0326326 | A1 | 12/2009 | Lin et al. |
| 2012/0022546 | A1* | 1/2012 | Hubschman ....... A61F 9/00754 606/107 |
| 2012/0035467 | A1* | 2/2012 | Lichtenstein ......... A61B 5/062 600/424 |
| 2012/0089014 | A1 | 4/2012 | Sabczynski et al. |
| 2012/0223937 | A1* | 9/2012 | Bendall ............... G06T 7/62 345/419 |
| 2013/0072917 | A1 | 3/2013 | Kaschke et al. |
| 2013/0077048 | A1 | 3/2013 | Mirlay |
| 2013/0102922 | A1 | 4/2013 | Gooding et al. |
| 2013/0317417 | A1* | 11/2013 | Claus ................... A61M 3/00 604/246 |
| 2014/0024969 | A1 | 1/2014 | Govari et al. |
| 2014/0320621 | A1 | 10/2014 | Sonnenschein et al. |
| 2014/0364870 | A1* | 12/2014 | Alvarez ............... A61B 3/10 606/130 |
| 2016/0030240 | A1 | 2/2016 | Gonenc et al. |
| 2016/0101263 | A1* | 4/2016 | Blumenkranz ...... A61B 5/6852 600/117 |
| 2017/0164869 | A1* | 6/2017 | Lee ................. A61B 1/00147 |
| 2019/0000563 | A1 | 1/2019 | Schneider et al. |
| 2019/0070395 | A1 | 3/2019 | Govari et al. |
| 2020/0107701 | A1 | 4/2020 | Gliner et al. |
| 2021/0093177 | A1* | 4/2021 | Anderson ............... A61B 1/05 |
| 2021/0145642 | A1* | 5/2021 | Berlin ................. A61B 90/361 |
| 2022/0257416 | A1* | 8/2022 | Foulkes .............. A61B 3/0008 |

OTHER PUBLICATIONS

Yu Y.Z., et al., "Endoscopy-assisted Vitrectomy in the Anterior Vitreous," International Journal of Ophthalmology, 2018, vol. 11 (3), pp. 506-511.

Cheng T., et al., "Innovative Surgical Endoscopes in Video-Assisted Thoracic Surgery," Journal of Thoracic Disease, Apr. 2018, vol. 10 (Suppl 6), pp. S749-S755.

Endoeye Flex 3D (LTF-190-10-3D) | Olympus America | Medical, https://medical.olympusamerica.com/products/laparoscopes/endoeye-flex-3d, 2020, 2 pages.

Francis B.A., et al., "Endoscopic Ophthalmic Surgery of the Anterior Segment," Survey of Ophthalmology, Mar.-Apr. 2014, vol. 59 (2), pp. 217-231.

* cited by examiner

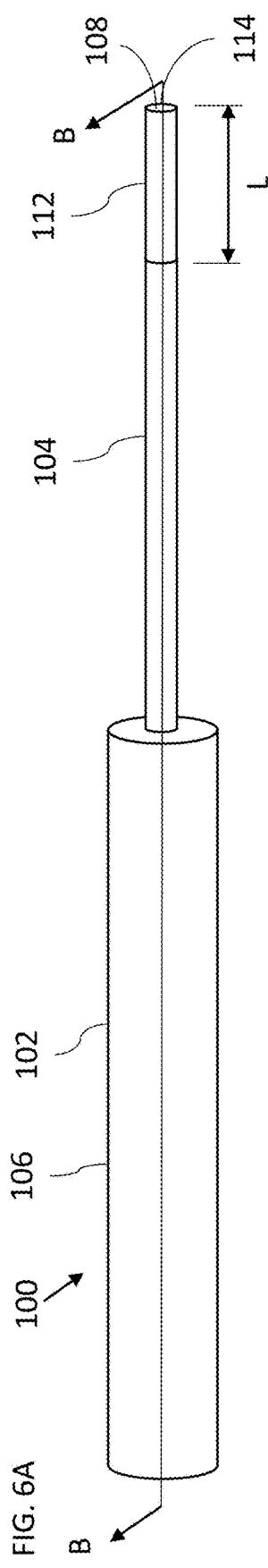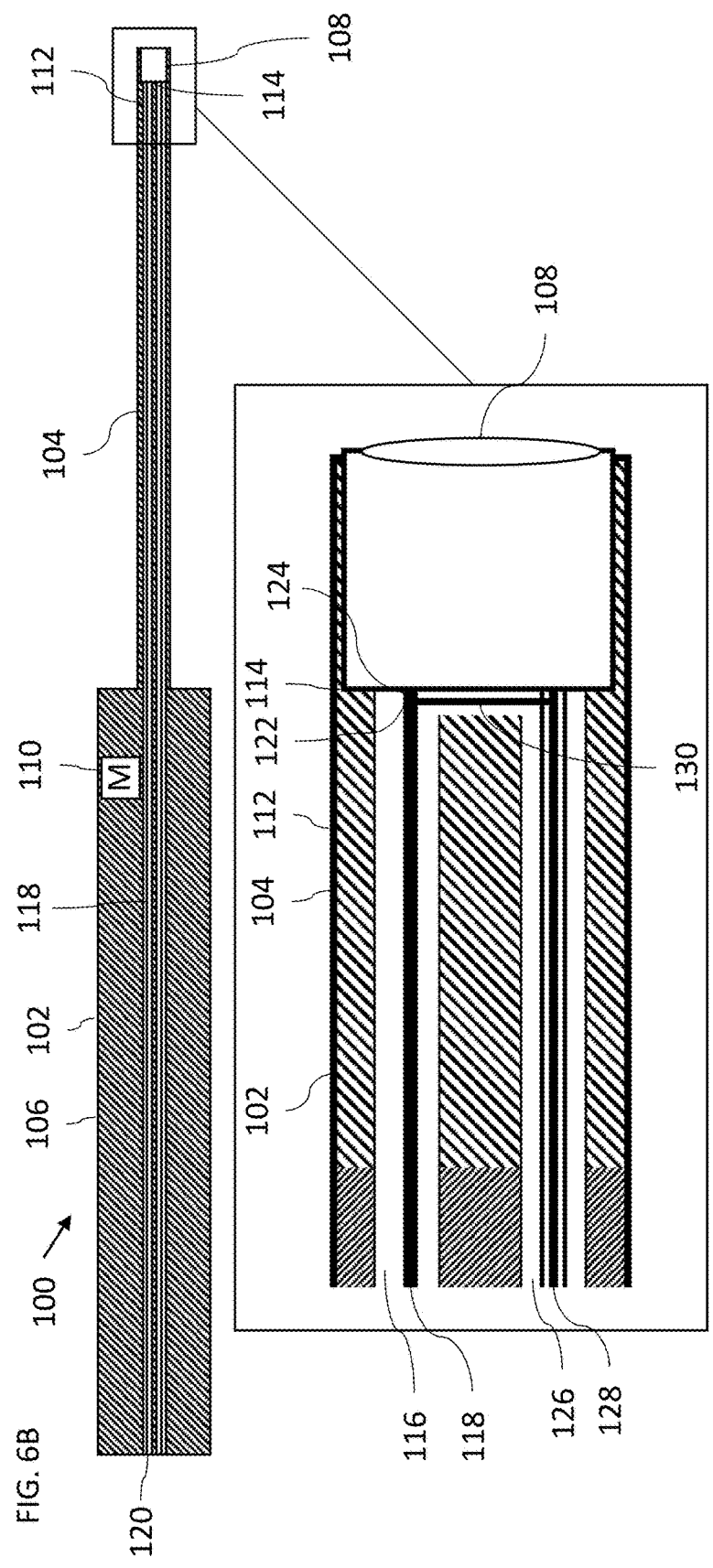

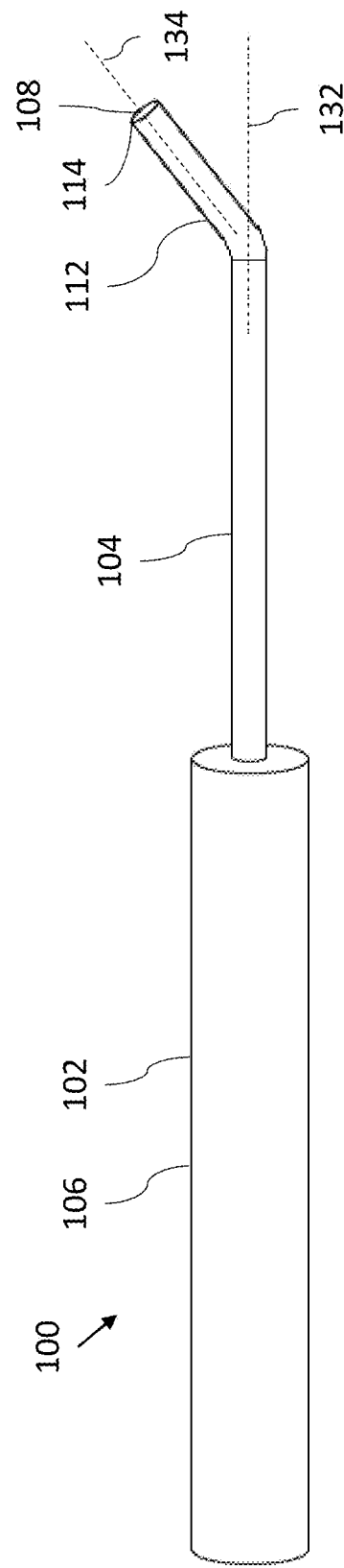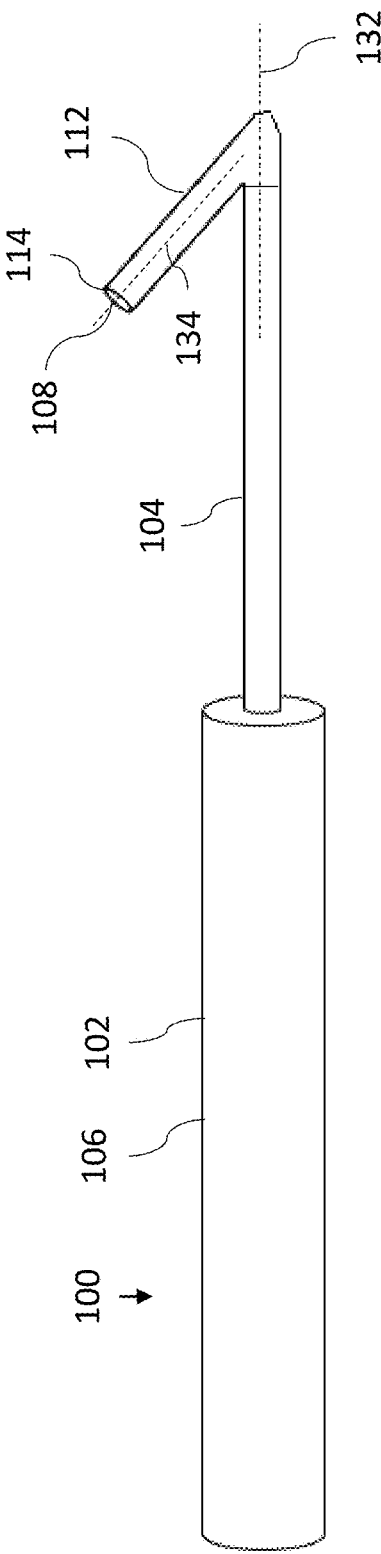

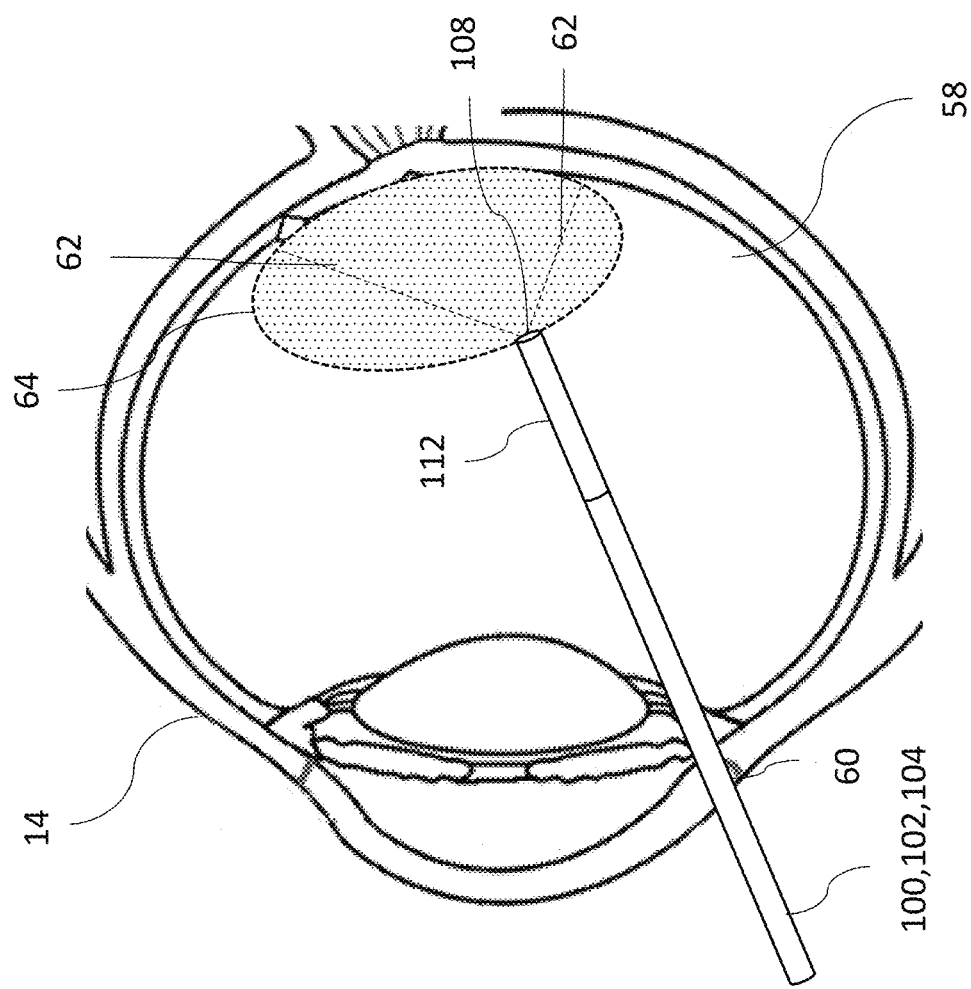
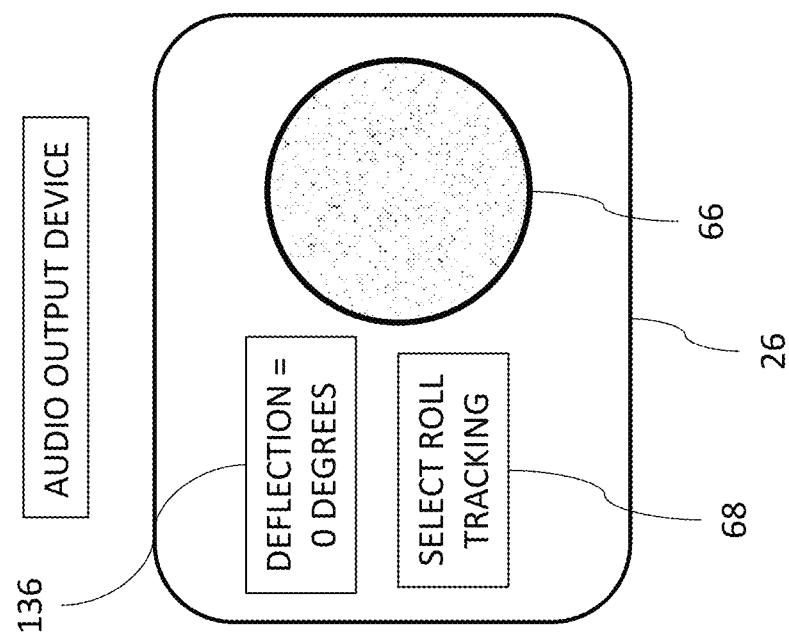
FIG. 8A

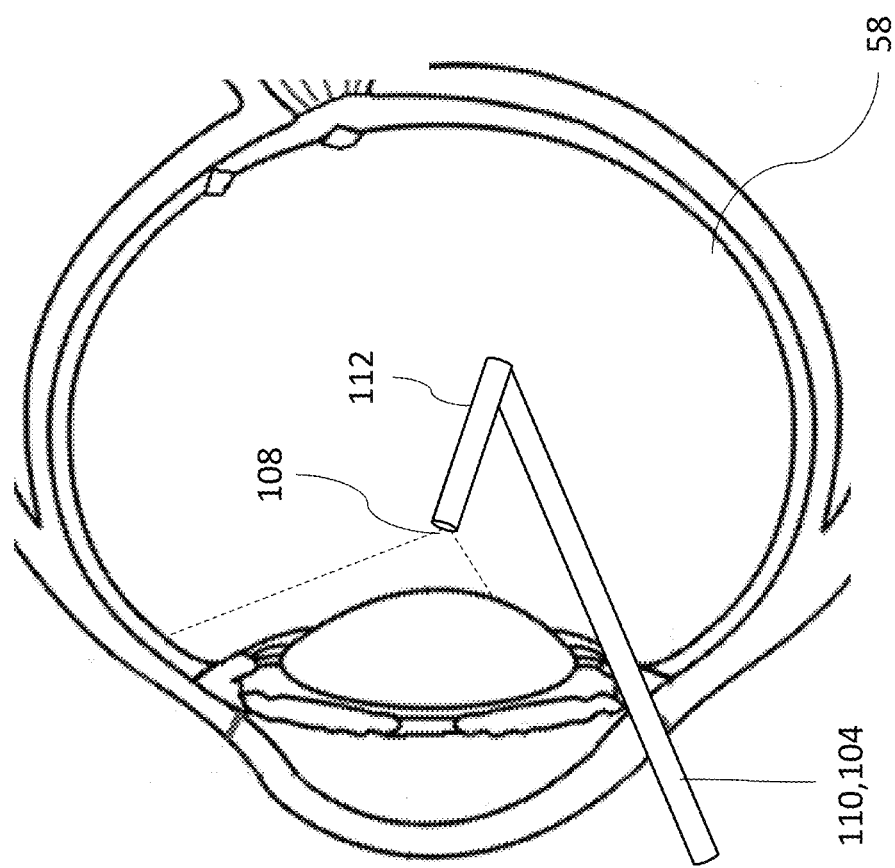
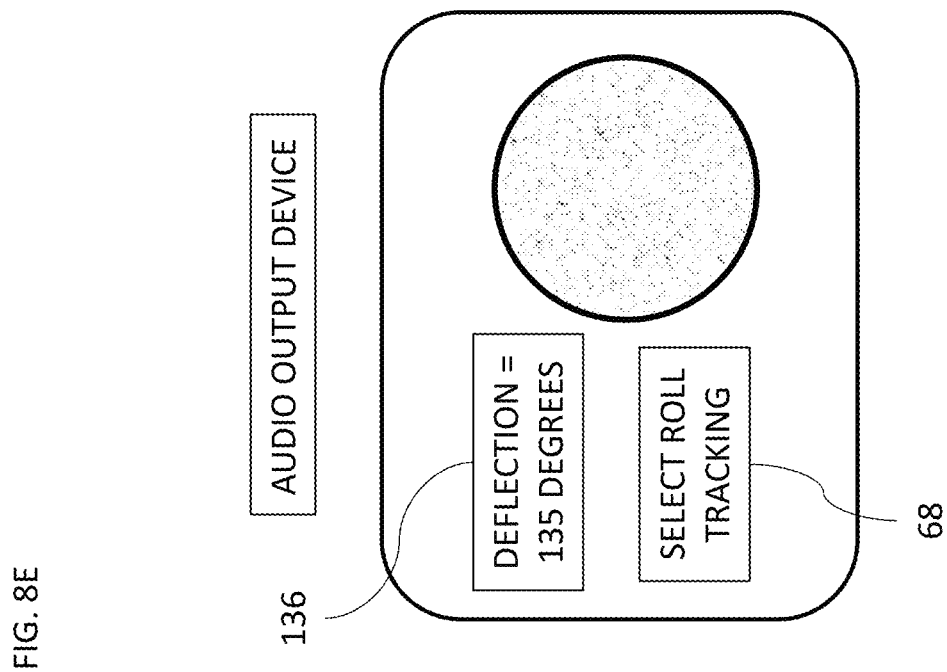
FIG. 8E

142 — COMPUTE DEFLECTION OF DEFLECTABLE ELEMENT

↓

144 — RENDER TO THE DISPLAY AN INDICATION OF THE COMPUTED DEFLECTION

148 — CAPTURE IMAGE

↓

150 — LABEL IMAGE WITH COMPUTED ROLL VALUE AND DEFLECTION

↓

152 — RENDER CAPTURED IMAGES ON 3D SURFACE REPONSIVELY TO COMPUTED DEFLECTION AND ROLL VALUES

156 — RECEIVE USER INTERFACE COMMAND TO ROTATE 3D SURFACE

↓

158 — RENDER ROTATED VIEW OF 3D SURFACE

EYE EXAMINATION APPARATUS

FIELD OF THE INVENTION

The present invention relates to medical equipment, and in particular, but not exclusively, to an eye examination apparatus.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Pressure may also be applied to increase the internal pressure within the eye. This lowers the chances of complications later in the surgery. Then a small incision is made in the cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates particles from the cataract through the tip. The pump is typically controlled with a microprocessor. The pump may be a peristaltic or a venturi type of pump. Aspirated fluids are replaced with irrigation of a balanced salt solution to maintain the anterior chamber of the eye. After removing the cataract with phacoemulsification, the softer outer lens cortex is removed with suction. An Intraocular lens (IOL) is introduced with the phacoemulsification probe through its needle into the empty lens capsule and the IOL unfolds. Small struts may hold the IOL in place. Once correctly installed the IOL restores the patient's vision.

In most cases, cataract surgery is performed without complication. However, in some eyes, the cataract cannot be removed completely and fragments of the cataract may fall into the back of the eye. Even the most skilled cataract surgeons have this happen, especially when the cataract is very firm or if trauma or other conditions have damaged the attachment of the lens to the inner wall of the eye. When cataract pieces or lens fragments remain in the eye after surgery, a severe inflammatory reaction can occur that may cause high pressure in the eye, swelling in the center of the retina and cornea, and even potentially permanent visual loss. In these cases, additional surgery is performed by a vitreoretinal surgeon who can safely retrieve the cataract fragments from the back of the eye. Proper timing of either medical or surgical follow-up care is crucial in providing the best possible outcome from this complication of cataract surgery.

U.S. Pat. No. 7,563,242 to Yaguchi, et al., describes an ultrasonic surgery apparatus capable of setting surgical conditions properly in accordance with the hardness of a nucleus lentis and performing surgery with efficiency. The ultrasonic surgery apparatus includes an ultrasonic vibration inducing unit, having an ultrasonic chip which induces ultrasonic vibrations to fragment and emulsify a nucleus lentis, an input unit which inputs a judgment result of hardness of the nucleus lentis, and a setting unit which sets a condition of the ultrasonic vibrations thereafter based on the inputted judgment result.

U.S. Pat. No. 8,708,488 to Kraus, et al., describes a method for carrying out eye surgery comprising a comparison of images recorded before surgery with images recorded during surgery in order to generate a marker which represents a target orientation of an intraocular lens or a difference between a current orientation and the target orientation of the intraocular lens. An eye surgery system respectively comprises an imaging system which is used during surgery and has a camera, and a diagnostic system which is used before surgery and which also has a camera. The imaging system used during surgery comprises an image processing device in order to perform a computation based on the recorded images, and in order to determine a respective orientation value, from which a representation of a marker representing the target orientation of the intraocular lens is obtained.

U.S. Pat. No. 9,962,226 to Brennan, et al., describes ophthalmic surgical systems, methods, and devices. In one embodiment, a surgical apparatus for use by a surgeon during a surgical procedure comprises one or more sealed sterilized surgical packs configured to be disposed of after a single or a limited number of surgical procedures, the one or more sealed sterilized surgical packs comprising: a sterile surgical instrument; and a sterile surgical tray comprising a top surface configured to be part of a sterile field of the surgical procedure, the top surface comprising a receiving structure for positioning therein of the sterile surgical instrument, the sterile surgical tray further comprising walls that define a recess sized and configured to receive a reusable non-sterile module, the recess configured to encapsulate the reusable non-sterile module to isolate the reusable non-sterile module from the sterile field of the surgical procedure.

U.S. Pat. No. 7,083,591 to Cionni describes a surge-flow regulator for use with an ophthalmic surgical instrument having an infusion line adapted to irrigate a surgical site with fluid and an aspiration line adapted to carry the fluid and particles of lenticular debris away from the surgical site. The surge-flow regulator includes a flow limiting device that is placed in fluid communication with the aspiration line to control surge-flow of the aspirated fluid and lenticular debris through the aspiration line. The lenticular debris carried in the aspiration line is processed into smaller particles before the fluid and debris are introduced to the flow limiting device.

U.S. Pat. No. 8,016,843 to Escaf describes an ophthalmologic cutting device having a base support section for attachment with a movement generating device and a tip with a blade section. The blade section preferably has upper and lower edges, and a forward aspiration free edge extending between them, with the upper edge having a shorter longitudinal length compared with the lower edge and where the forward edge slopes down from a distal end of the upper edge to a distal end of the lower edge, and the lower edge presenting a material contact surface that is thinner in thickness than the upper edge. A slope back in the proximal direction of the forward edge of, for example, 10 to 45 degrees with a straight and/or curving forward edge or a combination of a straight and forward edge sections is preferred. Embodiments of the blade include a blade converging in thickness from top to bottom and one having a curved upper forward edge region and one with a lower edge that has a distal straight section and a recessed section positioned proximal of said distal straight section. The forward edge is also preferably defined by longitudinally diverging, opposing side walls.

U.S. Pat. No. 9,498,377 to McCary et al., describes an ophthalmic surgical device that includes a housing having a distal end and a proximal end. A cannula is attached to the housing distal end and has a distal tip with at least one port in communication with a lumen extending through the cannula and in communication with an aspiration path in the housing. A vibration source is held within the housing for vibrating the distal tip for assisting in vitreous and other tissue removal. An aspiration source connected to the aspiration path for applying a negative pressure to the lumen and the at least one port for removing fluids and the vitreous and other tissue from the eye. The vibration source and the aspiration source together create a periodic bi-directional flow of tissue through the port without creating cavitation externally of the distal tip.

SUMMARY

There is provided in accordance with an exemplary embodiment of the present invention, an eye examination apparatus to inspect the vitreous humor of an eye, including a probe having a shaft comprising a distal end, a camera disposed at the distal end, wherein the distal end and the camera are configured to be inserted into the vitreous humor, and a magnetic orientation sensor disposed at a section of the shaft.

Further in accordance with an exemplary embodiment of the present invention the camera fits into a space of about a 1 mm cube or less.

Still further in accordance with an exemplary embodiment of the present invention the magnetic orientation sensor includes a magnetometer.

Additionally, in accordance with an exemplary embodiment of the present invention the probe includes a phacoemulsification probe including a needle at the distal end, the camera facing away from the shaft.

Moreover, in accordance with an exemplary embodiment of the present invention, the apparatus includes a pump connected to the needle and configured to aspirate a cataract fragment from the vitreous humor.

Further in accordance with an exemplary embodiment of the present invention the distal end of the shaft includes a distal tip, the camera being disposed within 5 mm of the distal tip.

Still further in accordance with an exemplary embodiment of the present invention the distal end of the shaft includes a deflectable element having a distal tip at which the camera is disposed, the magnetic orientation sensor being disposed in the shaft proximally to the deflectable element.

Additionally, in accordance with an exemplary embodiment of the present invention the distal end of the shaft has an outside diameter of less than 2 mm.

Moreover, in accordance with an exemplary embodiment of the present invention the deflectable element has a length of less than 5 mm and is configured to deflect by at least 120 degrees from an axis of a section of the shaft proximal to the deflectable element.

Further in accordance with an exemplary embodiment of the present invention, the apparatus includes a display, and processing circuitry configured to receive respective signals from the magnetic orientation sensor while the shaft is twisted to respective orientations, compute respective roll values of the shaft at the respective orientations responsively to the respective received signals, output a notification responsively to at least one of the computed roll values, and render to the display respective images captured by the camera of respective inside portions of the eye.

Still further in accordance with an exemplary embodiment of the present invention the processing circuitry is configured to find when one of the computed roll values exceeds a predefined limit, and output a notification indicating that the one computed role value exceeds the predefined limit.

Additionally in accordance with an exemplary embodiment of the present invention the distal end of the shaft includes a deflectable element having a distal tip at which the camera is disposed, the magnetic orientation sensor being disposed in the shaft proximally to the deflectable element, the processing circuitry being configured to compute a deflection of the deflectable element, and render to the display an indication of the computed deflection.

Moreover in accordance with an exemplary embodiment of the present invention the shaft includes a lumen and a puller wire having a proximal end and a distal end disposed in the lumen, the distal end of the puller wire being connected to the deflectable element so that pulling the proximal end of the puller wire in a proximal direction generates a deflection in the deflectable element, the processing circuitry being configured to compute the deflection of the deflectable element responsively to an impedance of at least part of the puller wire.

Further in accordance with an exemplary embodiment of the present invention the processing circuitry is configured to render to the display the respective images captured by the camera of the respective inside portions of the eye on a three-dimensional surface responsively to the computed deflection and the computed roll values, receive a user interface command to rotate the three-dimensional surface, and render to the display a rotated view of the three-dimensional surface responsively to the received user interface command.

There is also provided in accordance with another exemplary embodiment of the present invention an eye examination method to inspect a vitreous humor of an eye, including inserting a distal end of a shaft of a probe into the vitreous humor, the probe including a camera disposed at the distal end and a magnetic orientation sensor disposed at a section of the shaft, and rendering to a display respective images captured by the camera of respective inside portions of the eye.

Still further in accordance with an exemplary embodiment of the present invention, the method includes aspirating a cataract fragment from the vitreous humor.

Additionally, in accordance with an exemplary embodiment of the present invention, the method includes performing a pars plana vitrectomy to remove a cataract fragment from the vitreous humor.

Moreover, in accordance with an exemplary embodiment of the present invention, the method includes receiving respective signals from the magnetic orientation sensor while the shaft is twisted to respective orientations, computing respective roll values of the shaft at the respective orientations responsively to the respective received signals, and outputting a notification responsively to at least one of the computed roll values.

Further in accordance with an exemplary embodiment of the present invention, the method includes finding when one of the computed roll values exceeds a predefined limit, and outputting a notification indicating that the one computed role value exceeds the predefined limit.

Still further in accordance with an exemplary embodiment of the present invention, the method includes computing a deflection of a deflectable element of the shaft, the camera being disposed at a distal tip of the deflectable element, the magnetic orientation sensor being disposed in the shaft proximally to the deflectable element, and rendering to the display an indication of the computed deflection.

Additionally in accordance with an exemplary embodiment of the present invention computing the deflection includes computing the deflection of the deflectable element responsively to an impedance of at least part of a puller wire disposed in a lumen of the shaft and connected to the deflectable element so that pulling a proximal end of the puller wire in a proximal direction generates a deflection in the deflectable element.

Moreover in accordance with an exemplary embodiment of the present invention the rendering includes rendering to the display the respective images captured by the camera of the respective inside portions of the eye on a three-dimensional surface responsively to the computed deflection and the computed roll values, the method further including receiving a user interface command to rotate the three-dimensional surface and rendering to the display a rotated view of the three-dimensional surface responsively to the received user interface command.

BRIEF DESCRIPTION OF THE DRAWINGS

The present invention will be understood from the following detailed description, taken in conjunction with the drawings in which:

FIG. 6A is a schematic view of a probe for use with the apparatuses of FIGS. 1A and B;

FIG. 6B is a cross-section through line B-B of FIG. 6A;

FIGS. 7A and 7B are schematic views of the probe of FIG. 6A with different deflections;

FIGS. 8A-E are schematic views of a distal end of the probe of FIGS. 6A-B being used in an examination procedure;

FIGS. 10-12 are flowcharts including steps in methods of operation of the apparatuses of FIGS. 1A and 1B.

DESCRIPTION OF EXEMPLARY EMBODIMENTS

Overview

Figure 1A:
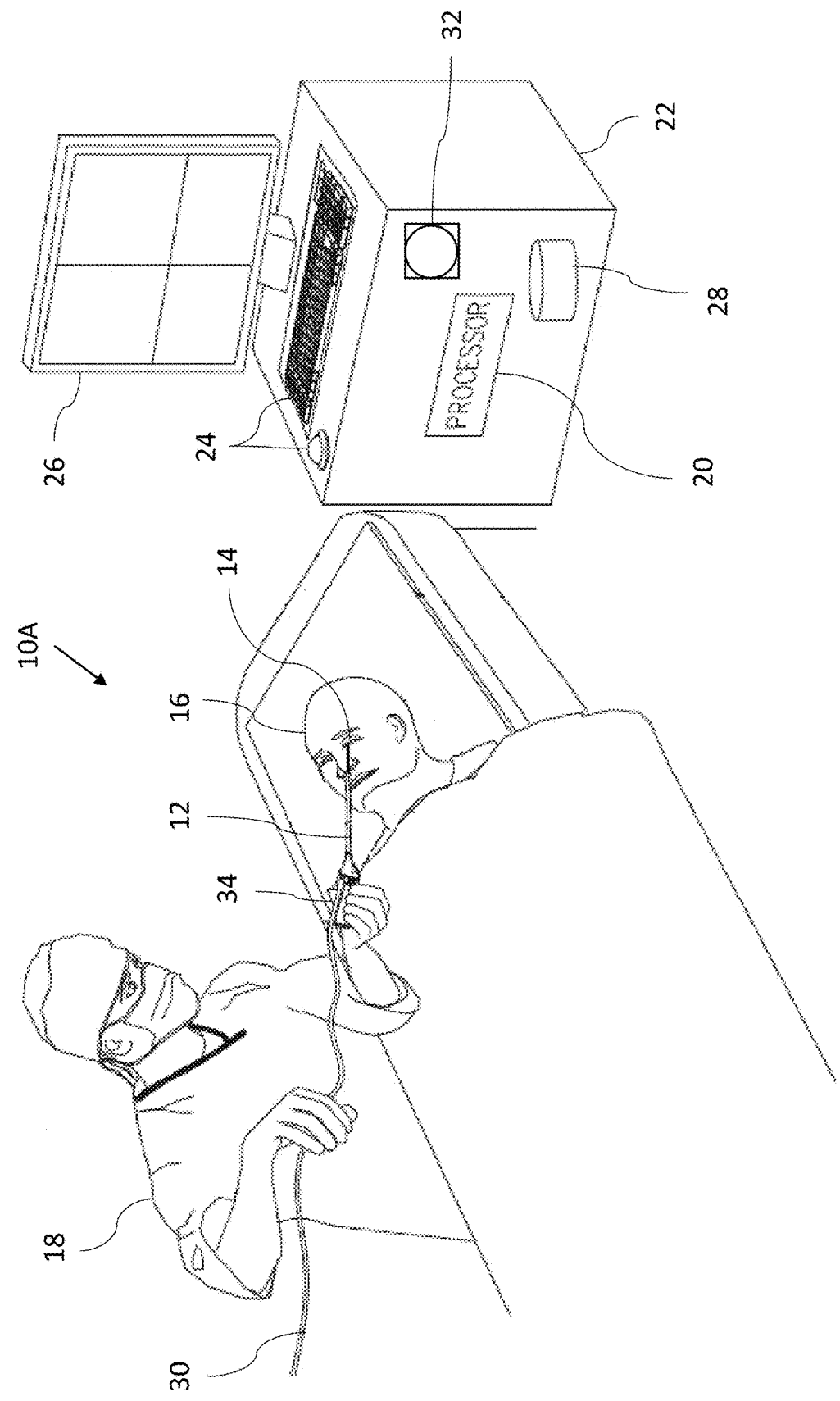
FIG. 1A is partly pictorial, partly block diagram view of an eye examination apparatus constructed and operative in accordance with an exemplary embodiment of the present invention.

As previously mentioned, when cataract pieces or lens fragments remain in the eye after surgery, a severe inflammatory reaction can occur that may cause high pressure in the eye, swelling in the center of the retina and cornea, and even potentially permanent visual loss. Additionally, or alternatively, the cataract or lens fragments may adhere to the IOL at least partially obscuring vision. At present the cataract or lens fragments generally only become apparent to the patient after the surgery has been completed, and apart from needing additional surgery to remove the cataract or lens fragments, the IOL may need to be removed and replaced.

Exemplary embodiments of the present invention solve the above problems by providing an eye examination apparatus including a probe which is inserted into the eye after a cataract procedure has been performed to search for cataract or lens fragments. The probe includes a camera which captures images in the vitreous humor as the probe is rotated. The probe includes a magnetic orientation sensor which provides signals that may be used to compute a roll of the probe and thereby determine if the probe has been rotated completely, e.g., by 360 degrees, inside the eye. In some exemplary embodiments, the magnetic orientation sensor is a magnetometer which provides signals responsively to its orientation with respect to the earth's magnetic field. In other exemplary embodiments, the magnetic orientation sensor provides signals detected from a magnetic location pad placed near the head of the patient.

The camera used in the probe is generally very small, and in some exemplary embodiments, may fit in a 1 mm size cube. The magnetometer may have similar dimensions.

In some exemplary embodiments, the probe is implemented as part of a phacoemulsification probe including a needle at its distal end with the camera facing away from a shaft of the probe. When cataract or lens fragments are found in the camera images, a pump may be used to aspirate the fragments from the vitreous humor. The camera is generally placed close to the distal tip of the probe, for example, within 5 mm of the distal tip.

In some exemplary embodiments, the probe is implemented separately from the phacoemulsification probe and includes at its distal end a deflectable element having a distal tip at which the camera is placed. The magnetic orientation sensor is placed in the shaft of the probe proximally to the deflectable element. The distal end of the shaft may have an outside diameter of less than 2 mm, for example, 1 mm. In some exemplary embodiments, the deflectable element may have a length of less than 5 mm and deflect by at least 120 degrees (e.g., up to 180 degrees) from an axis of the section of the shaft proximal to the deflectable element. The shaft of the probe may include a lumen and a puller wire placed in the lumen with the distal end of the puller wire connected to the deflectable element so that pulling the proximal end of the puller wire in a proximal direction generates a deflection in the deflectable element. Deflecting the deflectable element allows the physician to angle the camera to different portions of the interior of the eye. For example, if the camera has a field of view of 90 degrees, the deflectable element of the probe may be deflected to about 45 degrees and then the probe is twisted 360 degrees so that the camera may capture about half of the interior of the eye as the probe is being twisted. The deflectable element may then be deflected to about 135 degrees and then the probe is twisted 360 degrees so that the camera may capture the other half of the interior of the eye as the probe is being twisted. Processing circuitry computes the deflection of the deflectable element using any suitable method for example, responsively to an impedance of at least part of the puller wire, because the impedance increases as the wire is stretched.

In some exemplary embodiments, the processing circuitry receives respective signals from the magnetic orientation sensor while the shaft is twisted to respective orientations and computes respective roll values of the shaft at the respective orientations responsively to the respective received signals. The processing circuitry outputs a notification responsively to one or more of the computed roll values. For example, the computed roll values may be rendered to a display. Additionally, the processing circuitry may render to the display respective images captured by the camera of respective inside portions of the eye. The processing circuitry finds when one of the computed roll values exceeds a predefined limit (e.g., 360 degrees) and outputs a notification (e.g., visual, audio, and/or tactile) indicating that the computed role exceeds the predefined limit. In exemplary embodiments where the probe includes the deflectable element, the processing circuitry may also render to the display an indication of the computed deflection. For example, "deflection equals 45 degrees."

In some exemplary embodiments, the captured images may be rendered to a three-dimensional (3D) surface such as a sphere according to the computed roll values and deflections at which the respective captured images were captured. The 3D surface may then be manipulated by a user to see different sides of the 3D surface.

System Description

Reference is now made to FIG. 1A, which is partly pictorial, partly block diagram view of an eye examination apparatus 10A constructed and operative in accordance with an embodiment of the present invention. The eye examination apparatus 10A is configured to inspect a vitreous humor of an eye.

The eye examination apparatus 10A comprises a probe 12 configured for insertion into an eye 14 of a patient 16 by a physician 18. The probe 12 may include a camera (not shown) disposed at its distal end and a magnetic orientation sensor (not shown). The magnetic orientation sensor may include a magnetometer which provides signals when its orientation is changed with respect to the earth's magnetic field.

The probe 12 comprises a handle 34 which may include controls to control among other functions a deflection of a deflectable element at the distal end of the probe 12 when the probe 12 include a deflectable element.

Images captured by the camera, and signals provided by magnetic orientation sensor are processed by a processor 20 included in a console 22 of the eye examination apparatus 10A. The console 22 comprises operating controls 24 that typically include a keypad and/or a pointing device such as a mouse or trackball.

The physician 18 uses operating controls 24 to interact with the processor 20 while performing the eye inspection procedure. While performing the procedure, the processor 20 may present results of the procedure on a display 26. Processor 20 also termed "processing circuitry" may use software stored in a memory 28 to operate the eye examination apparatus 10A. In practice, some or all of the functions of the processor 20 may be combined in a single physical component or, alternatively, implemented using multiple physical components. These physical components may comprise hard-wired or programmable devices, or a combination of the two. In some exemplary embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The probe 12 is connected to the console 22 via a cable 30 to convey electrical signals between the probe 12 and the console 22. In some exemplary embodiments, the console 22 includes a pumping system 32 to pump irrigation fluid to the distal end of the probe 12 and aspirate waste matter away from the distal end of the probe 12 via the cable 30.

In other exemplary embodiments, the probe 12 is connected wirelessly to the console 22 to convey electrical signals between the probe 12 and the console 22.

Figure 1B:
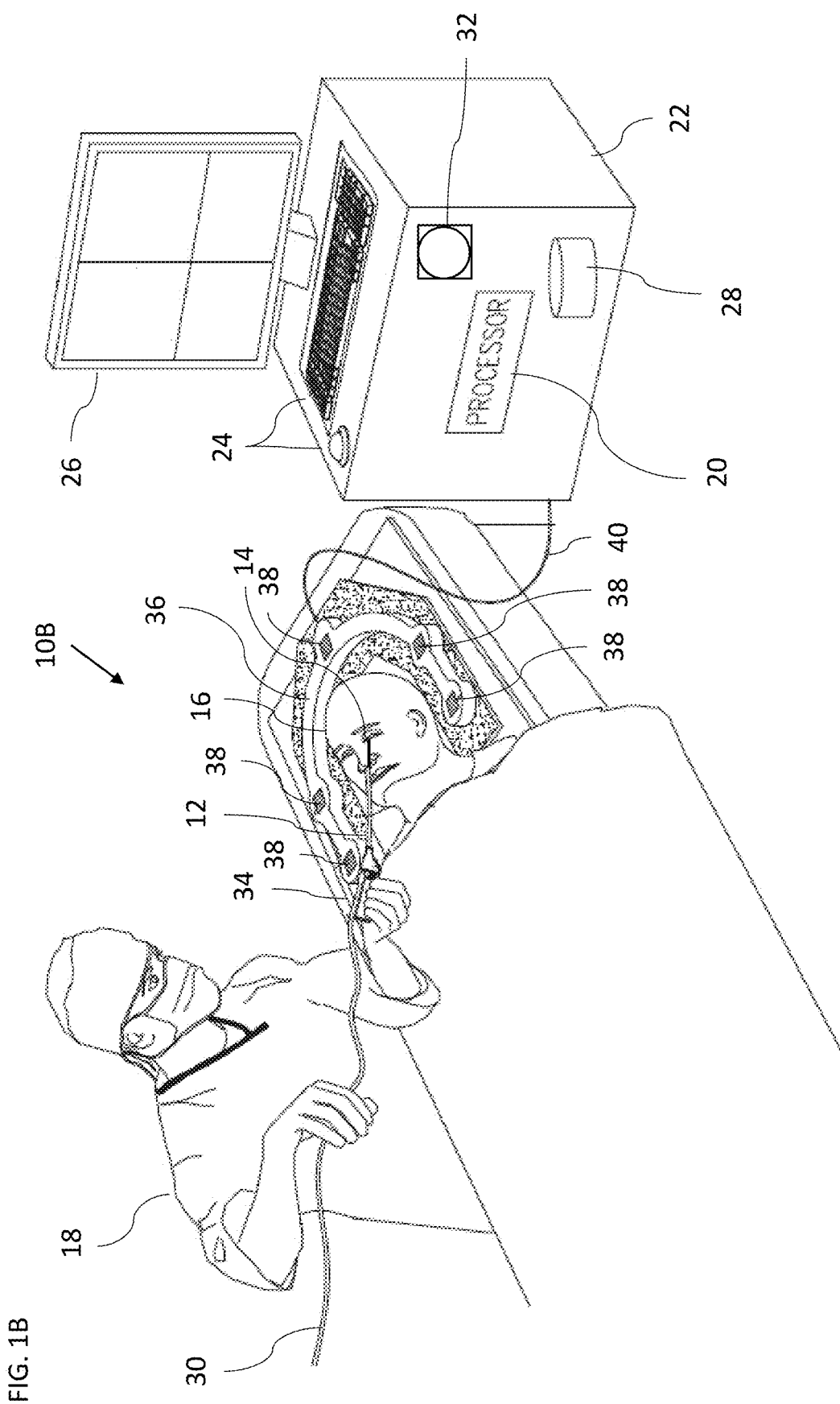
FIG. 1B is partly pictorial, partly block diagram view of an eye examination apparatus constructed and operative in accordance with an alternative exemplary embodiment of the present invention.

Reference is now made to FIG. 1B, which is partly pictorial, partly block diagram view of an eye examination apparatus 10B constructed and operative in accordance with an alternative exemplary embodiment of the present invention. The eye examination apparatus 10B is substantially the same as the eye examination apparatus 10A except for the following differences.

The magnetic orientation sensor of probe 12 may comprise one or more magnetic sensors, typically single, dual and/or triple axis coils, that are tracked during the procedure by a magnetic tracking system. In some exemplary embodiments, for the tracking to be effective, frames of reference of a CT (computerized tomography) image of the patient 16 and of the magnetic tracking system, are registered. While the CT image may typically comprise a magnetic resonance imaging (MRI) image or a fluoroscopic image, in the description herein the image is assumed to comprise, by way of example, a fluoroscopic CT image.

Prior to and during the eye procedure, a magnetic radiator assembly 36, also called a location pad, comprised in the magnetic tracking system, is positioned beneath, or around, the patient's head. The magnetic radiator assembly 36 comprises magnetic field radiators 38 which are fixed in position and which transmit alternating magnetic fields into a region wherein the head of patient 16 is located. Potentials generated by a magnetic sensor in region 30, in response to the magnetic fields, enable the position and/or the orientation of the sensor to be measured in the magnetic tracking system's frame of reference. The console 22 may be connected to the magnetic field radiators 38 via one or more cables 40 and/or wirelessly.

By way of example, radiators 38 of assembly 36 are arranged in an approximately horseshoe shape around the head of patient 16. However, alternate configurations for the radiators of assembly 36 will be apparent to those having ordinary skill in the art, for example, the magnetic field radiators 38 may be arranged in a collar arrangement placed around the neck of the patient 16, and all such configurations are assumed to be comprised within the scope of the present invention.

In some exemplary embodiments, prior to the procedure, the registration of the frames of reference of the magnetic tracking system with the CT image may be performed by positioning a magnetic sensor at known positions, such as the tip of the patient's nose, of the image. However, any other convenient system for registration of the frames of reference may be used. Elements of system 10B, including radiators 38 and sensor, are under overall control of the processor 20.

Figure 2:
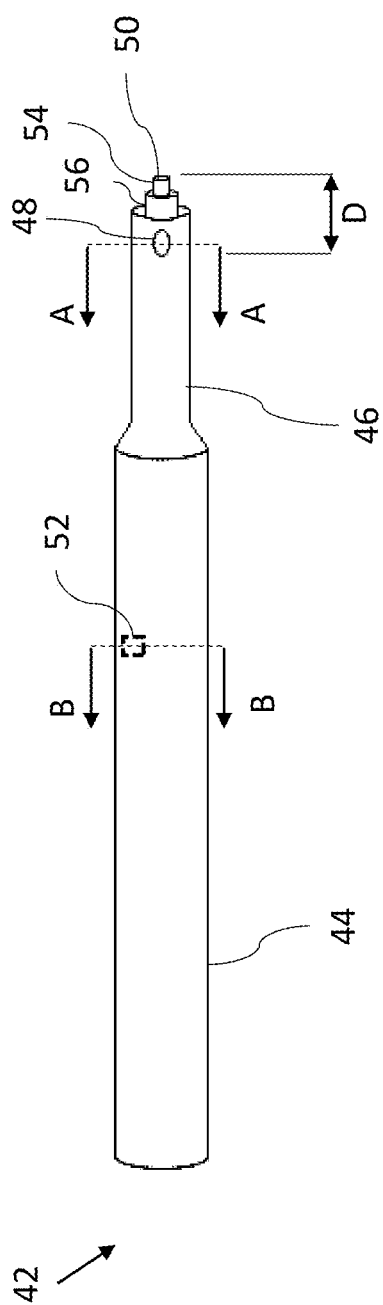
FIG. 2 is a schematic view of a phacoemulsification probe for use with the apparatuses of FIGS. 1A and 1B.
Figure 3B:
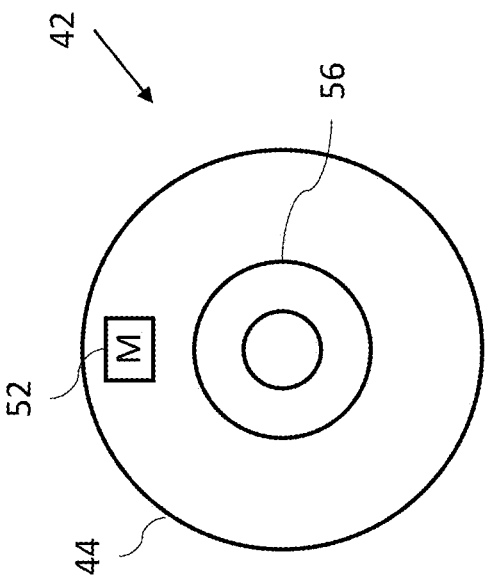
FIGS. 3A and 3B are cross-sectional views of the probe of FIG. 2 through lines A-A and B-B of FIG. 2, respectively.
Figure 3A:
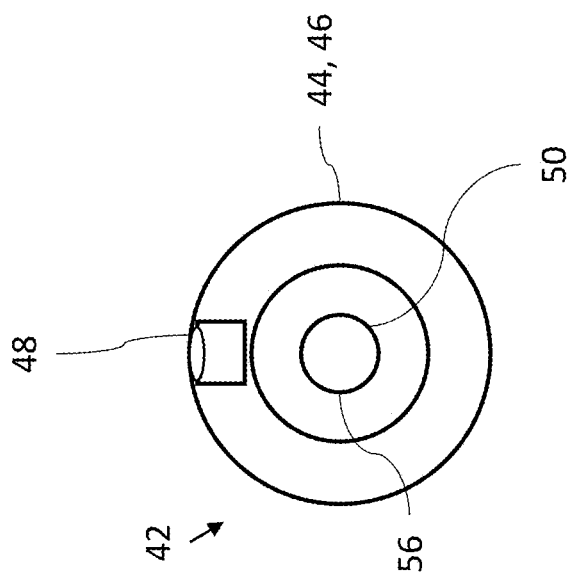

Reference is now made to FIGS. 2, 3A and 3B. FIG. 2 is a schematic view of a phacoemulsification probe 42 for use with the apparatuses 10A, 10B of FIGS. 1A and 1B. FIGS. 3A and 3B are cross-sectional views of the probe of FIG. 2 through lines A-A and B-B of FIG. 2, respectively. The phacoemulsification probe 42 may be used instead of the probe 12 of FIGS. 1A and 1B.

The phacoemulsification probe 42 includes a shaft 44 having a distal end 46, a camera 48 disposed at the distal end 46, a needle 50 disposed at the distal end 46, and a magnetic orientation sensor 52 disposed at a section of the shaft 44. The distal end 46 and the camera 48 are configured to be inserted into the vitreous humor of the eye 14 (FIGS. 1A-B). The outer diameter of the distal end 46 may be any suitable value. In some exemplary embodiments, the outer diameter of the distal end 46 is about 3 mm.

The camera 48 may be disposed in the shaft 44 with a transparent or translucent window between the camera 48 and the outside of the shaft 44. Alternatively, the camera 48 may be placed level with the outside surface of the shaft 44. Alternatively, the camera 48 may be disposed outside of the shaft 44 and optionally covered with a transparent or translucent sleeve, such as a shrink sleeve. The camera 48 faces away from the shaft 44 so that a field of view of the camera 48 faces away from the shaft 44. In some exemplary embodiments, an axis of the field of view in generally perpendicular to the axis of the shaft 44. The field of view of the camera 48 may nevertheless face in any suitable direction. In some exemplary embodiments, the phacoemulsification probe 42 may include two or more cameras fixed at different angles with respect to the shaft 44. The distal end 46 of the shaft 44 includes a distal tip 54. In some exemplary embodiments, the camera 48 is disposed within 5 mm of the distal tip 54. In some exemplary embodiments, the camera 48 fits into a space of about a 1 mm cube or less. Any suitable camera may be used for the camera 48, for example, OVM6948 which has package dimensions of 650×650× 1158 micrometers, and is commercially available from Omnivision® of Santa Clara, CA, USA or NanEye®, with a footprint of 1 mm×1 mm and a field of view of 90, 120, or 160 degrees. NanEye is commercially available from ams AG, Tobelbader Strasse 30, 8141 Premstaetten, Austria.

The magnetic orientation sensor 52 may be disposed in or on the shaft 44 and optionally covered with a sleeve, such as a shrink sleeve. In some exemplary embodiments, the magnetic orientation sensor 52 includes a magnetometer, which provides a measure of roll of the phacoemulsification probe 42 with respect to the earth's magnetic field. For example, ROHM Semiconductor of Kyoto Japan provides BM1422AGMV Digital Magnetometer IC with 2 mm×2 mm×1 mm dimensions. STMicroelectronics, Geneva, Switzerland provides LSM303AGR and LIS3MDL magnetometer with the same dimensions. In some embodiments, the magnetic orientation sensor 52 includes single, dual, and/or triple axis coils which provide signals responsively to signals provided by the magnetic field radiators 38 of FIG. 1B.

The pumping system 32 (FIGS. 1A-B) may include a pump connected to the needle 50 and configured to aspirate a cataract fragment from the vitreous humor of the eye 14 (FIGS. 1A-B). The phacoemulsification probe 42 also includes an irrigation channel 56 which may be disposed around, or adjacent to, the needle 50. The irrigation channel 56 is also connected to the pumping system 32. The phacoemulsification probe 42 may include other items (not shown) such as, an ultrasonic unit to drive the needle 50.

Figure 4A:
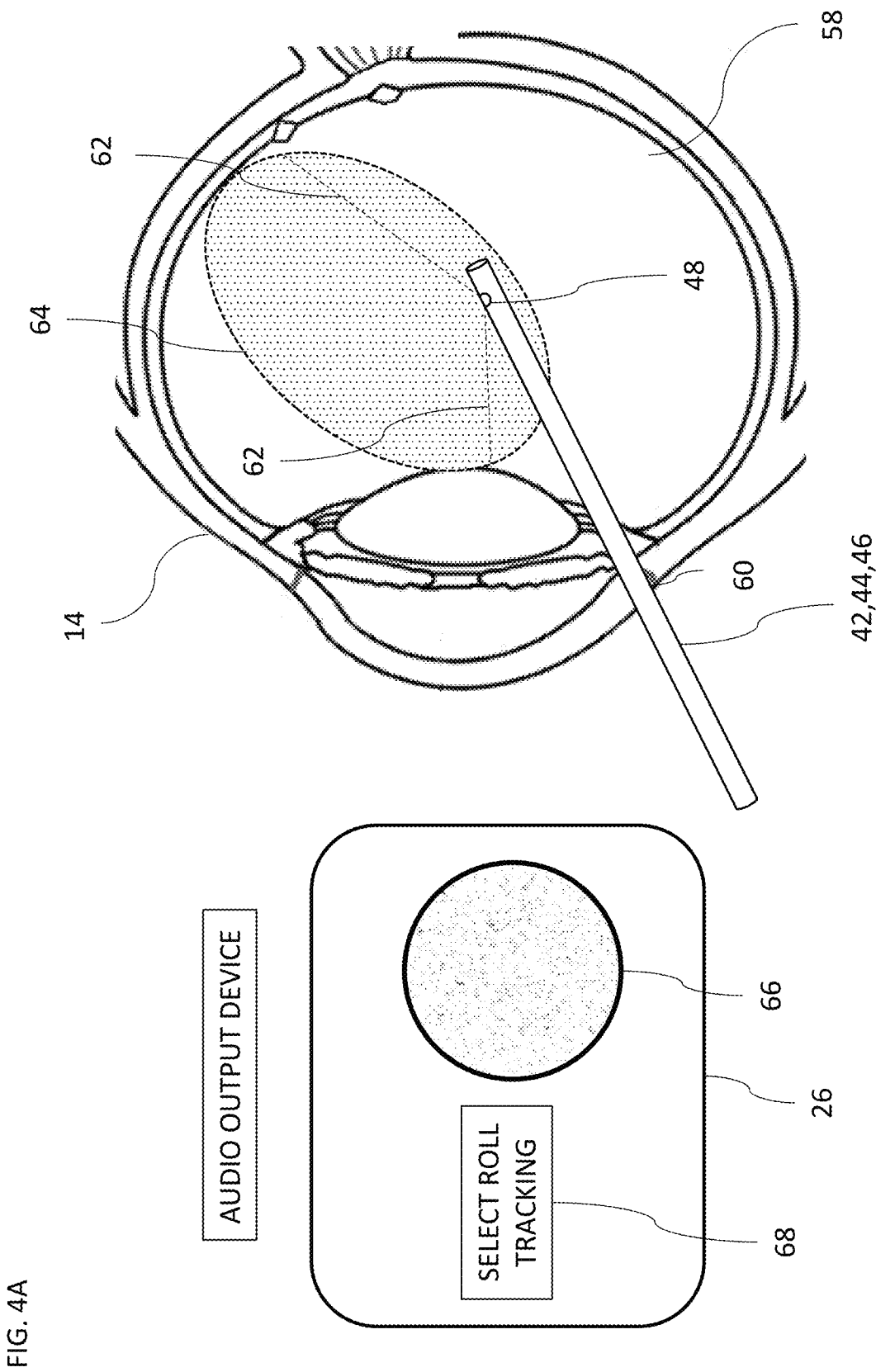
FIGS. 4A-C are schematic views of a distal end of the probe of FIG. 2 being used in an examination procedure.
Figure 4B:
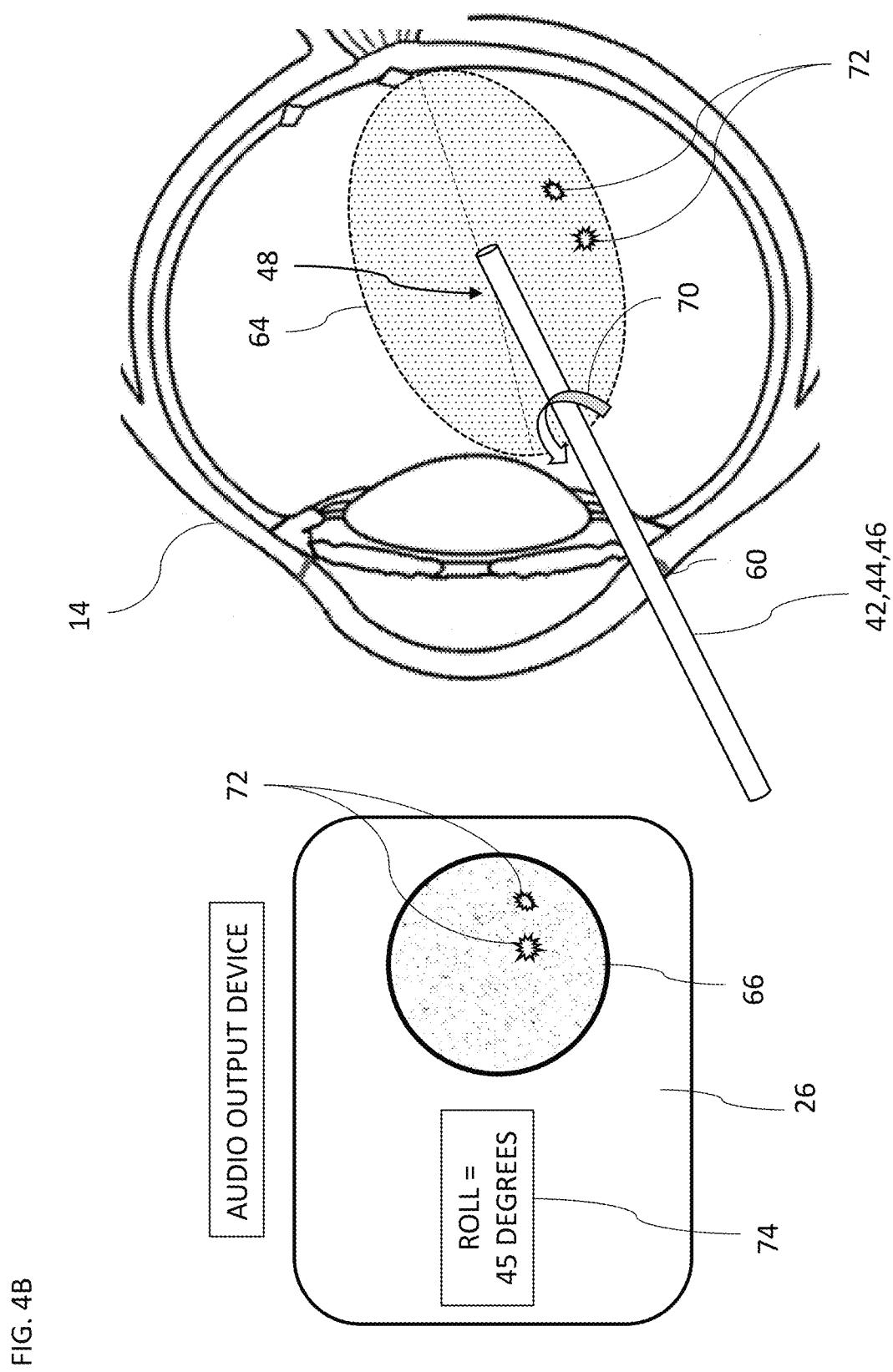
Figure 4C:
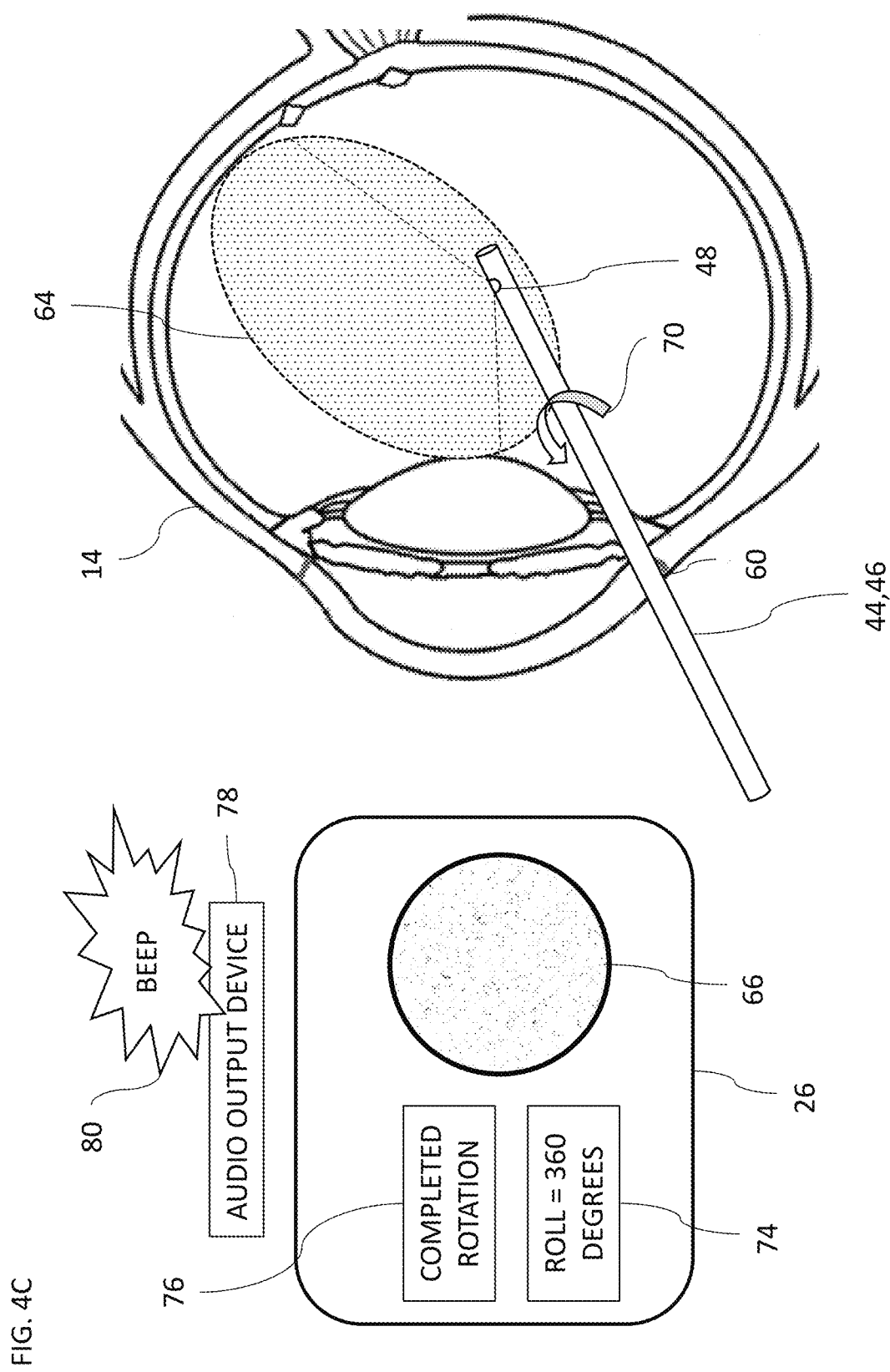

Reference is now made to FIGS. 4A-C, which are schematic views of the distal end 46 of the probe 42 of FIG. 2 being used in an examination procedure. FIG. 4A shows the distal end 46 of the shaft 44 inserted into a vitreous humor 58 of the eye 14 via an incision 60 made during the cataract surgery. The field of view of the camera 48 is shown by way of lines 62 and an image footprint 64. An image 66 captured by the camera 48 is displayed on the display 26. The display 26 also displays a button 68 which has been selected by the physician 18 (FIGS. 1A-B) to start roll tracking.

FIG. 4B shows that the distal end 46 of the shaft 44 has been rotated by 45 degrees in an anti-clockwise direction, as indicated by an arrow 70. The image footprint 64 has also moved to a new position in the eye 14 and includes cataract fragments 72 as reflected in the image 66 captured by the camera 48 and displayed on the display 26. The display 26 also includes an indication 74 of the current roll of the distal end 46 of the shaft 44 with respect to the original orientation of the shaft 44 when the physician 18 selected to start roll tracking. The current roll is computed responsively to signals provided by the magnetic orientation sensor 52 (FIG. 2) using any suitable roll computation method.

FIG. 4C shows that the distal end 46 of the shaft 44 has been rotated by an addition 315 degrees in an anti-clockwise direction, as indicated by the arrow 70, so that the shaft 44 has been rotated by 360 degrees since roll tracking was started. The image footprint 64 has returned to its original position shown in FIG. 4A. The indication 74 of the current roll of the shaft 44 shows that the current roll of the distal end 46 of the shaft 44 with respect to the original orientation of the shaft 44 when the physician 18 selected to start roll tracking is 360 degrees. The display 26 also includes an additional indication 76 indicating that the shaft 44 has completed a full rotation. Additionally, or alternatively, an audio output device 78 may output an audible signal 80 when the shaft 44 has completed the full rotation. In some embodiments, the full rotation may be indicated using tactile feedback, for example, by vibrating the handle 34 (FIGS. 1A-B).

The amount of the interior of the eye captured by the camera 48 when the shaft 44 is rotated 360 degrees depends on the field of view of the camera 48. For example, if the field of view of the camera 48 is 160 degrees, then even though a majority of the interior of the eye 14 should be captured, a portion of the interior of the eye 14 may not be captured when rotating the shaft 44 by 360 degrees. If the shaft 44 is subsequently tilted by 20 degrees and then rotated by 360 degrees again, the remaining portion of the interior of the eye may be captured by the camera 48. The images captured by the camera 48 may be saved as a video which may be replayed by the physician 18 (FIG. 1) to inspect the video for the fragments 72 (FIG. 4B).

Figure 5:
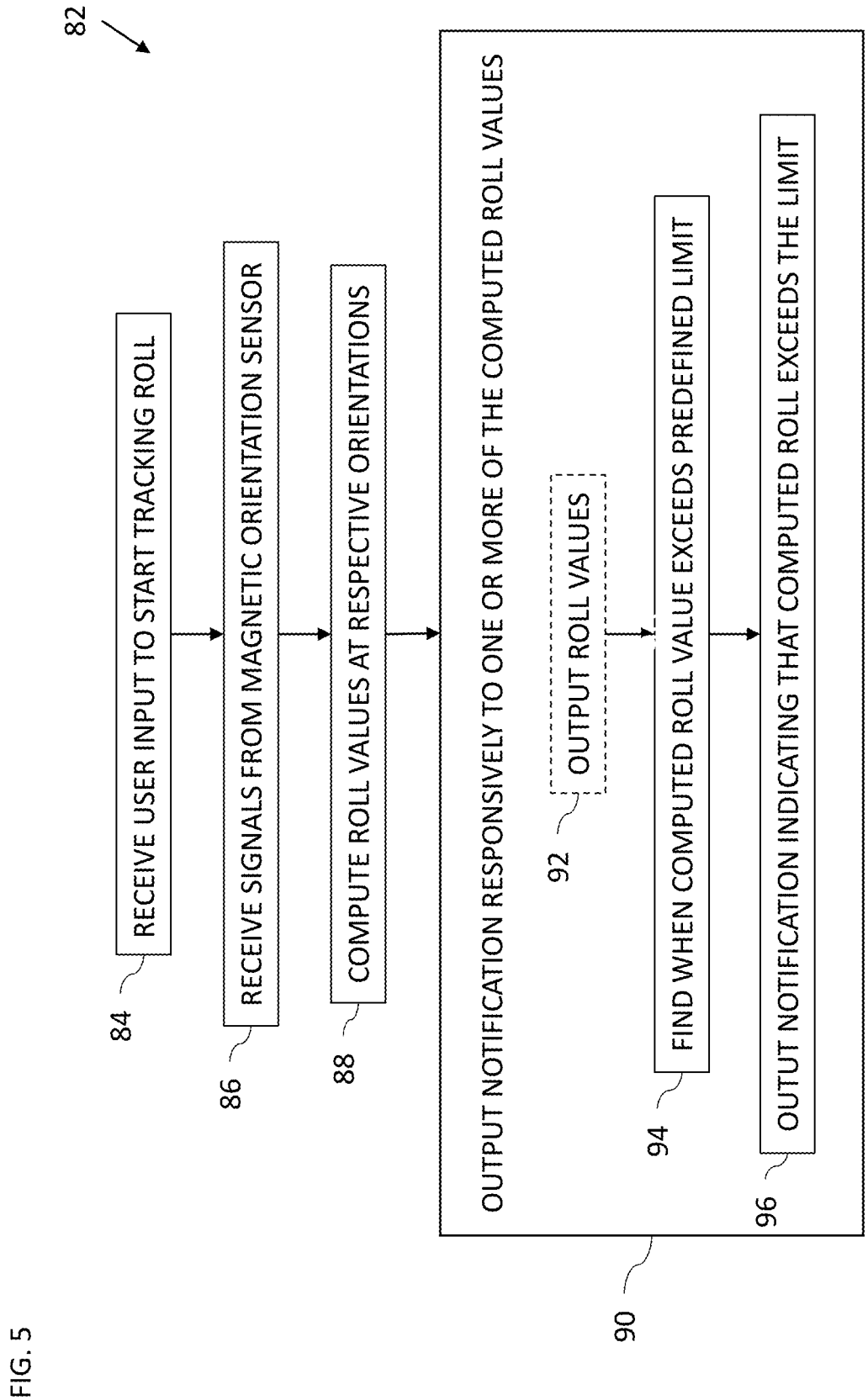
FIG. 5 is a flowchart including steps in method of operation of the apparatuses of FIGS. 1A and 1B.

Reference is now made to FIG. 5, which is a flowchart 82 including steps in method of operation of the apparatuses 10A and 10B of FIGS. 1A and 1B.

The processor 20 (FIGS. 1A-B) is configured to receive (block 84) user input to start roll tracking of the distal end 46 of the shaft 44 of the phacoemulsification probe 42 (FIG. 2). The processor 20 is configured to receive (block 86) respective signals from the magnetic orientation sensor 52 (FIG. 2) while the shaft is twisted to respective orientations. The processor 20 is configured to compute (block 88) respective roll values of the shaft 44 at the respective orientations responsively to the respective received signals. The roll values are computed with respect to a current roll orientation of the shaft from an original orientation of shaft when the roll tracking was started.

The processor 20 is configured to output (block 90) a notification responsively to one or more of the computed roll values. The notification may include displaying the current roll value of the shaft 44 and/or when the computed roll value exceeds a predefined limit such as 360 degrees.

Steps of blocks 92-96 described below are sub steps of block 90.

The processor 20 is optionally configured to output (block 92) the computed roll values while the shaft 44 is being rotated. The processor 20 is configured to find (block 94)

when one of the computed roll values exceeds the predefined limit, such as 360 degrees. The processor 20 is configured to output (block 96) a notification indicating that one of the computed role values exceeds the predefined limit. The notification may include audio, a display and/or tactile feedback to indicate that the computed role value has exceeded the predefined limit.

In addition to the above steps, the camera 48 (FIG. 2) is configured to capture images. The processor 20 is configured to render to the display 26 (FIGS. 1A-B) respective images captured by the camera 48 of respective inside portions of the eye 14 (FIGS. 1A-B). When fragment(s) 72 (FIG. 4B) are found, they may be removed by aspirating the cataract fragment(s) 72 from the vitreous humor 58 (FIG. 4A) using the phacoemulsification probe 42 or another tool or by performing a pars plana vitrectomy to remove the cataract fragment(s) 72 from the vitreous humor 58.

Reference is now made to FIGS. 6A-B and 7A-B. FIG. 6A is a schematic view of a probe 100 for use with the apparatuses 10A and 10B of FIGS. 1A and B. FIG. 6B is a cross-section through line B-B of FIG. 6A. FIGS. 7A and 7B are schematic views of the probe 100 of FIG. 6A with different deflections. The probe 100 may be used instead of the probe 12 of FIGS. 1A and 1B.

The probe includes a shaft 102 including a distal end 104 and a proximal end 106, a camera 108 disposed at the distal end 104, and a magnetic orientation sensor 110 (FIG. 6B) disposed at a section of the shaft 102. The distal end 104 and the camera 108 are configured to be inserted into a vitreous humor of the eye 14 (FIGS. 1A-B). The proximal end 106 remains outside of the eye during the examination procedure.

The distal end 104 of the shaft 102 includes a deflectable element 112 having a distal tip 114 at which the camera 108 is disposed. The center of field of view of the camera 108 is generally parallel to an axis of the deflectable element 112. The magnetic orientation sensor 110 is disposed in the shaft 102 proximally to the deflectable element 112. The magnetic orientation sensor 110 may be disposed in the distal end 104 or the proximal end 106.

In some exemplary embodiments, the camera 108 fits into a space of about a 1 mm cube or less. Any suitable camera may be used for the camera 108, for example, OVM6948 which has package dimensions of 650×650×1158 micrometers, and is commercially available from of Omnivision® of Santa Clara, CA, USA or NanEye®, which is a miniature sized image sensor with a footprint of 1 mm×1 mm and a field of view of 90, 120, or 160 degrees. NanEye is commercially available from ams AG, Tobelbader Strasse 30, 8141 Premstaetten, Austria.

In some exemplary embodiments, the magnetic orientation sensor 110 includes a magnetometer, which provides a measure of roll of the probe 100 with respect to the earth's magnetic field. For example, ROHM Semiconductor of Kyoto Japan provides BM1422AGMV Digital Magnetometer IC with 2 mm×2 mm×1 mm dimensions. STMicroelectronics, Geneva, Switzerland provides LSM303AGR and LIS3MDL magnetometer with the same dimensions. In some embodiments, the magnetic orientation sensor 110 includes single, dual, or triple axis coils which provide signals responsively to signals provided by the magnetic field radiators 38 of FIG. 1B.

The distal end 104 may have any suitable outside diameter. In some exemplary embodiments, the distal end 104 of the shaft 102 has an outside diameter of less than 2 mm, typically 1-2 mm. The proximal end 106 may have any suitable outside diameter, for example, but not limited to, 3 mm or more. The deflectable element 112 may have any suitable length L. In some exemplary embodiment, the deflectable element 112 has a length L of less than 5 mm, for example, 3 mm or less.

The deflectable element 112 may deflect by any suitable angle. In some exemplary embodiments, an axis 134 (FIGS. 7A, 7B) of the deflectable element 112 is configured to deflect by at least 120 degrees from an axis 132 (FIGS. 7A, 7B) of a section of the shaft 102 proximal to the deflectable element 112.

FIG. 6B shows that the shaft 102 includes a lumen 116 and a puller wire 118 having a proximal end 120 and a distal end 122 disposed in the lumen 116. The distal end 122 of the puller wire 118 is connected to a distal portion 124 of the deflectable element 112 so that pulling the proximal end 120 of the puller wire 118 in a proximal direction generates a deflection in the deflectable element 112 as shown in FIGS. 7A and 7B. The puller wire 118 may be implemented using any suitable material, for example, stainless steel or a nickel-titanium alloy. The deflectable element 112 may be configured as deflecting in one direction only, or in two directions by using more than one puller wire. The deflectable element 112 may be implemented using any suitable flexible biocompatible material such as polyimide or polyurethane. The deflectable element 112 may be resilient. The rest of the shaft 102 may be implemented using any suitable biocompatible material, for example, polyimide. The shaft 102 also includes a lumen 126 in which wires 128 connect the magnetic orientation sensor 110 and the camera 108 to the processor 20 (FIGS. 1A-B).

The angle of deflection between the axis 134 of the deflectable element 112 and the axis 132 of the section of the shaft 102 may be computed based on calibrating the angle of deflection as a function of the stretching of the puller wire 118. In some embodiments, the wires 128 may also include a connection 130 to the distal end 122 of the puller wire 118, and another electrical connection may be connected to the proximal end 120 of the puller wire 118 so that an impedance of the puller wire 118 (or a part thereof, such as a coating on the puller wire 118) may be measured, for example, by the processor 20 (FIGS. 1A-B), in order to determine angle of deflection of the deflectable element 112 as a function of impedance in the puller wire 118 or a part thereof. A controller on the handle 34 (FIGS. 1A and 1B) may be used to adjust the puller wire 118, which in turn adjusts the deflection. In some embodiments, a calibrated scale may be added to the controller or to the handle 34 showing the different angles of deflection that may be caused by certain adjustments of the controller.

Reference is now made to FIGS. 8A-E, which are schematic views of the distal end 104 of the probe 100 of FIGS. 6A-B being used in an examination procedure.

FIG. 8A shows the distal end 104 of the shaft 102 of the probe 100 inserted into the vitreous humor 58 of the eye 14 via the incision 60 made during the cataract surgery. The field of view of the camera 108 is shown by way of lines 62 and the image footprint 64. The image 66 captured by the camera 108 is displayed on the display 26. The display 26 is also displaying the button 68 which is selected by the physician 18 (FIGS. 1A-B) to start roll tracking, and an indication 136 of the angle of deflection of the deflectable element 112. At present, the deflectable element 112 is not deflected.

The examples of FIGS. 8A-E assume that the field of view of the camera 108 is about 90 degrees. However, the field of view of the camera 108 may be any suitable value less than 90 degrees or greater than 90 degrees. Therefore, rotating the shaft 102 of the probe 100 around 360 degrees with one deflection of the deflectable element 112 will only result in about half of the vitreous humor 58 being captured by the camera 108. The examples of FIGS. 8A-E describe the deflectable element 112 being deflected to 45 degrees (see FIGS. 8B-D) and then 135 degrees (see FIG. 8E), and at each deflection rotating the shaft 102 by 360 degrees to enable the camera 108 to capture most, if not all, of the vitreous humor 58. Instead of deflecting the deflectable element 112 to two positions, the deflectable element 112 may be deflected to more than two positions, and then rotated by 360 degrees at each deflection.

Figure 8B:
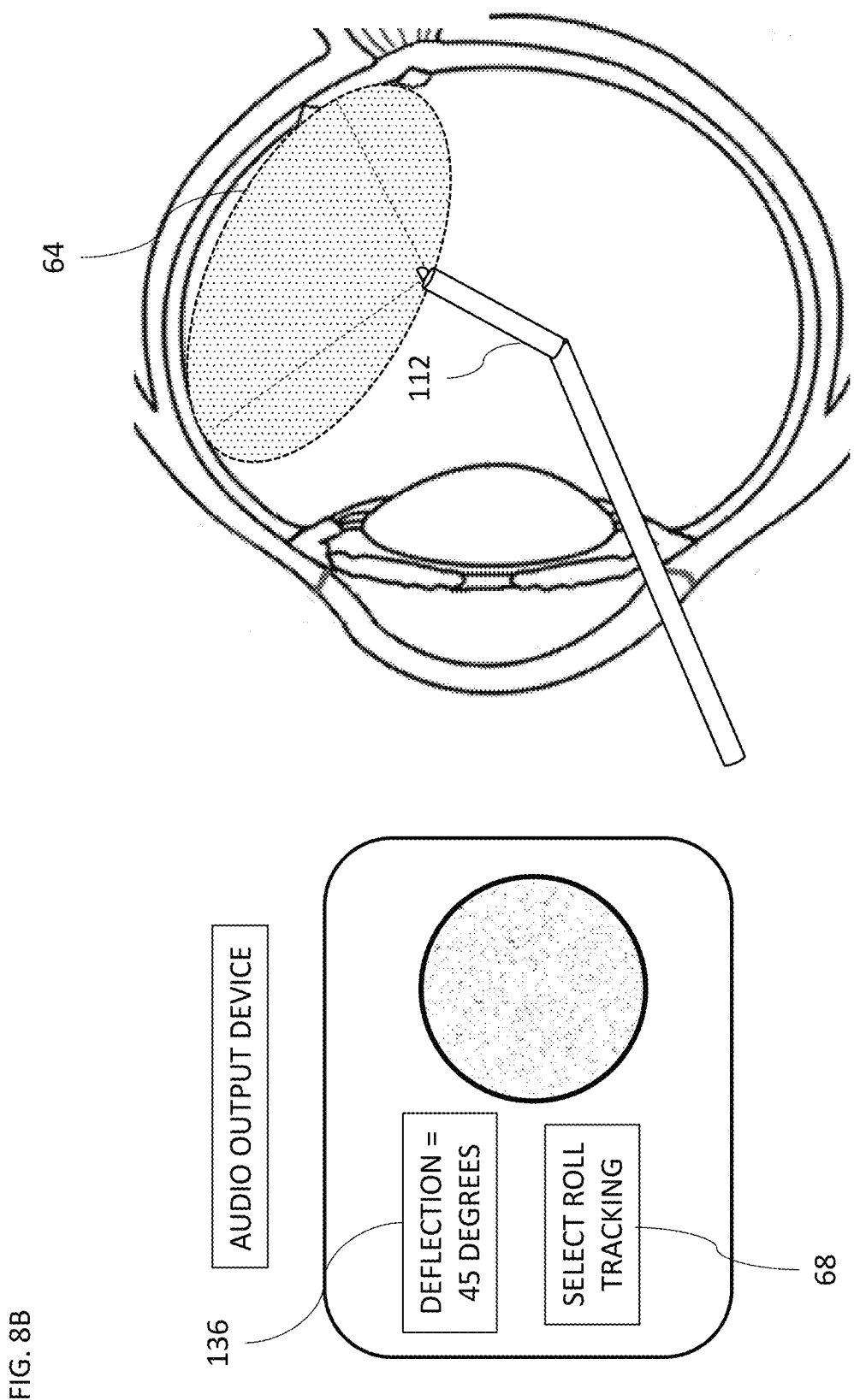

FIG. 8B shows that deflectable element 112 is deflected to 45 degrees as indicated by the indication 136. The image footprint 64 also moves accordingly to the deflection of the deflectable element 112. The button 68 is selected by the physician 18 to start roll tracking.

Figure 8C:
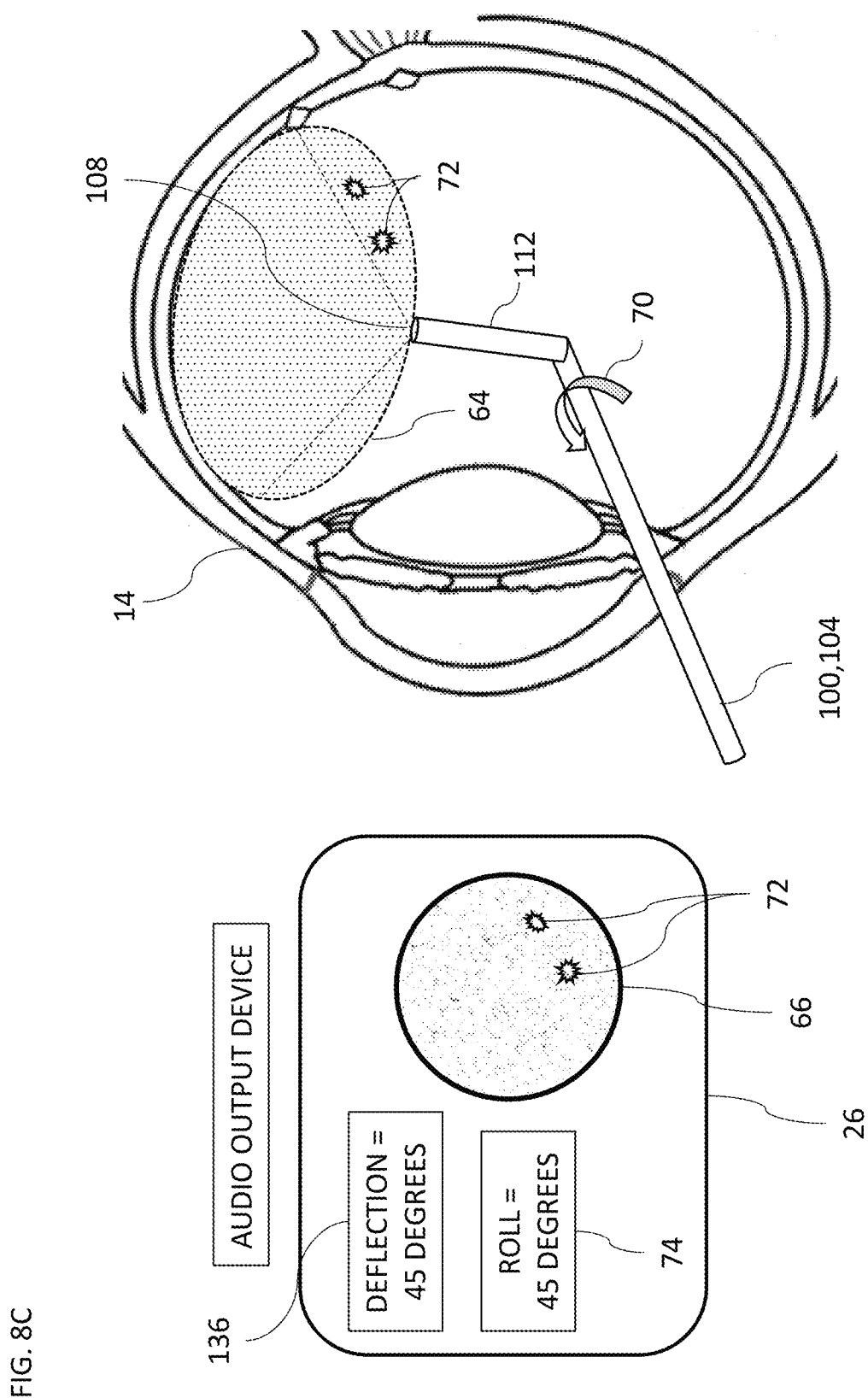

FIG. 8C shows that the distal end 104 of the probe 100 including the deflectable element 112 has been rotated by 45 degrees in an anti-clockwise direction, as indicated by the arrow 70. The image footprint 64 has also moved to a new position in the eye 14 and includes cataract fragments 72 as reflected in the image 66 captured by the camera 108 and displayed on the display 26. The display 26 also includes the indication 74 of the current roll of the distal end 104 with respect to the original orientation of the probe 100 when the physician 18 selected to start roll tracking. The current roll is computed responsively to signals provided by the magnetic orientation sensor 110 (FIG. 6B) using any suitable roll computation method.

Figure 8D:
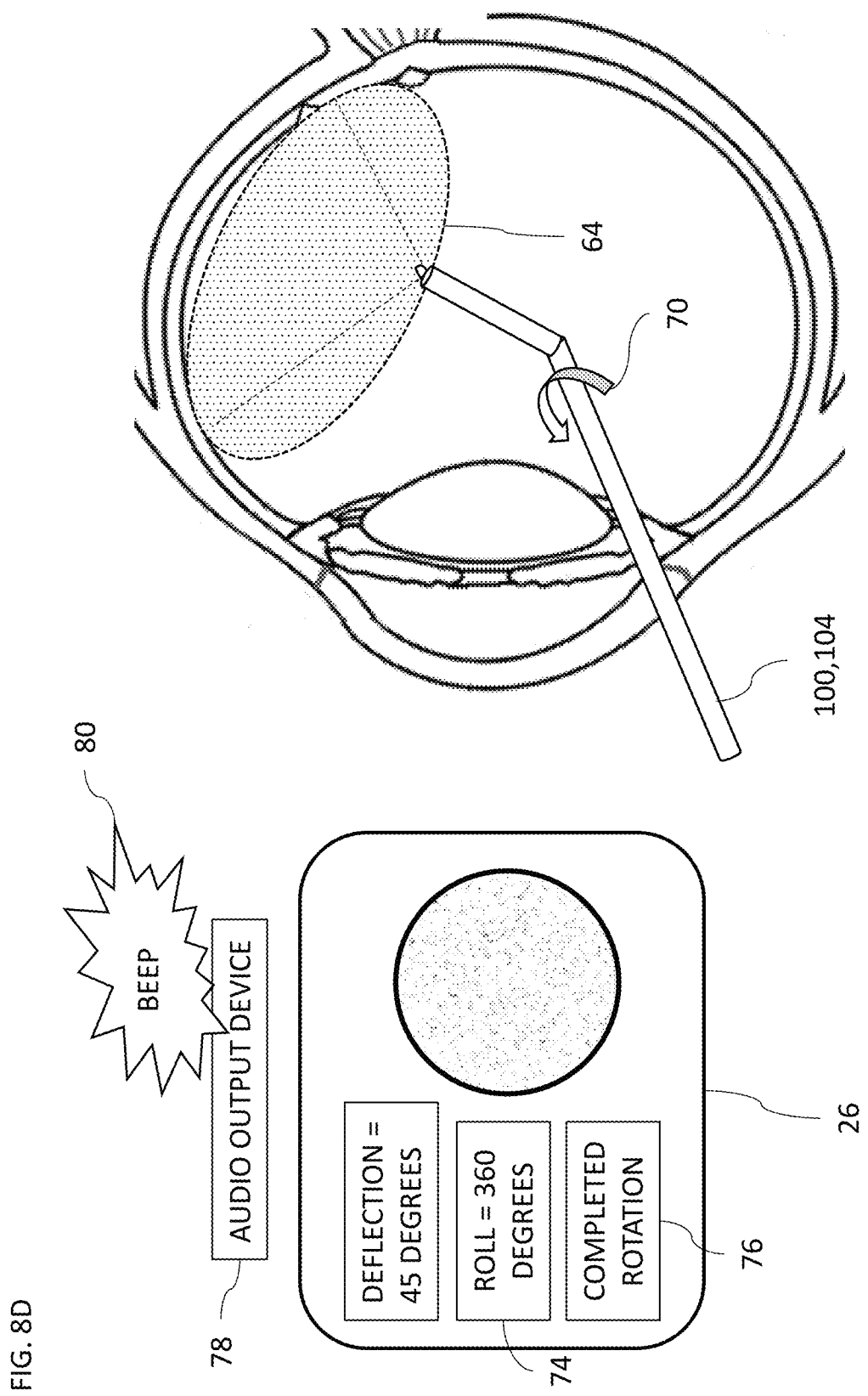

FIG. 8D shows that the distal end 104 of the probe 100 has been rotated by an addition 315 degrees in an anti-clockwise direction, as indicated by the arrow 70, so that the probe 100 has been rotated by 360 degrees since roll tracking was started. The image footprint 64 has returned to its original position shown in FIG. 8B. The indication 74 of the current roll of the probe 100 shows that the current roll of the distal end 104 with respect to the original orientation of the distal end 104 when the physician 18 selected to start roll tracking is 360 degrees. The display 26 also includes the additional indication 76 indicating that the distal end 104 has completed a full rotation. Additionally, or alternatively, the audio output device 78 may output audible signal 80 when the distal end 104 has completed the full rotation. In some embodiments, the full rotation may be indicated using tactile feedback, for example, by vibrating the handle 34 (FIGS. 1A-B).

FIG. 8E shows that the deflectable element 112 has been deflected further to a deflection of 135 degrees as indicated on the indication 136. The button 68 is selected by the physician 18 to start roll tracking again. The distal end 104 of the probe 100 is then rotated 360 degrees while the camera 108 captures images of the vitreous humor 58 at this deflection of the deflectable element 112.

The method described with reference to FIG. 5 may also be used, with suitable changes, for the probe 100. If fragment(s) 72 are found with the probe 100, the fragment(s) 72 may subsequently be aspirated from the vitreous humor 58 with a phacoemulsification probe or another aspiration probe or by performing a pars plana vitrectomy to remove the cataract fragment(s) 72 from the vitreous humor 58.

Figure 9B:
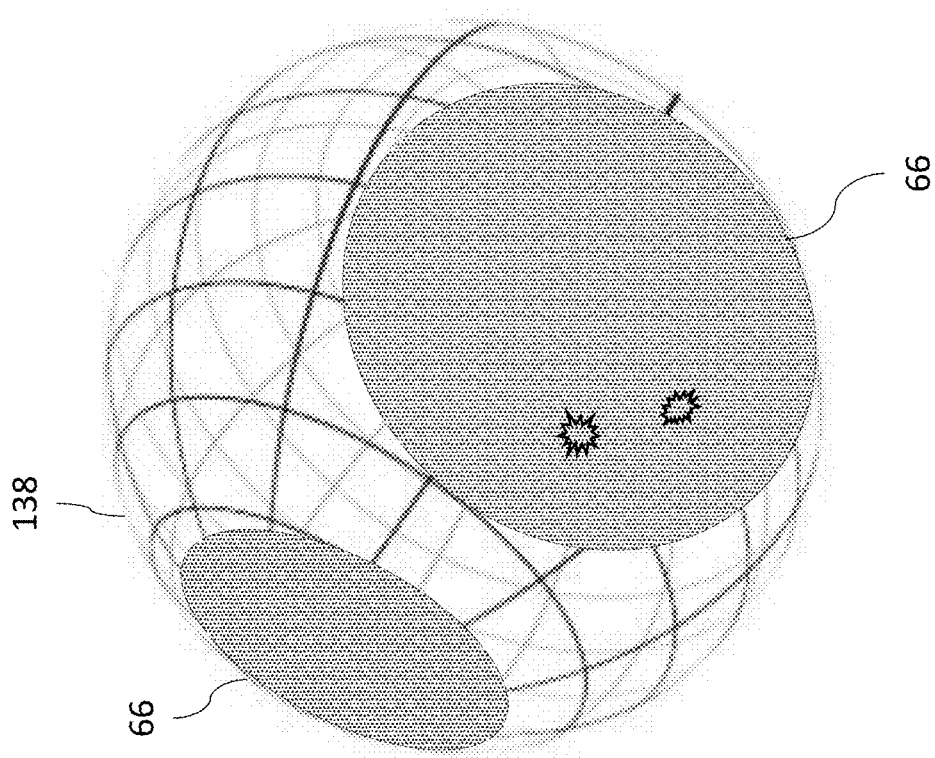
FIGS. 9A-C are schematic views of a three-dimensional surface for use in the apparatuses of FIGS. 1A and 1B.
Figure 9A:
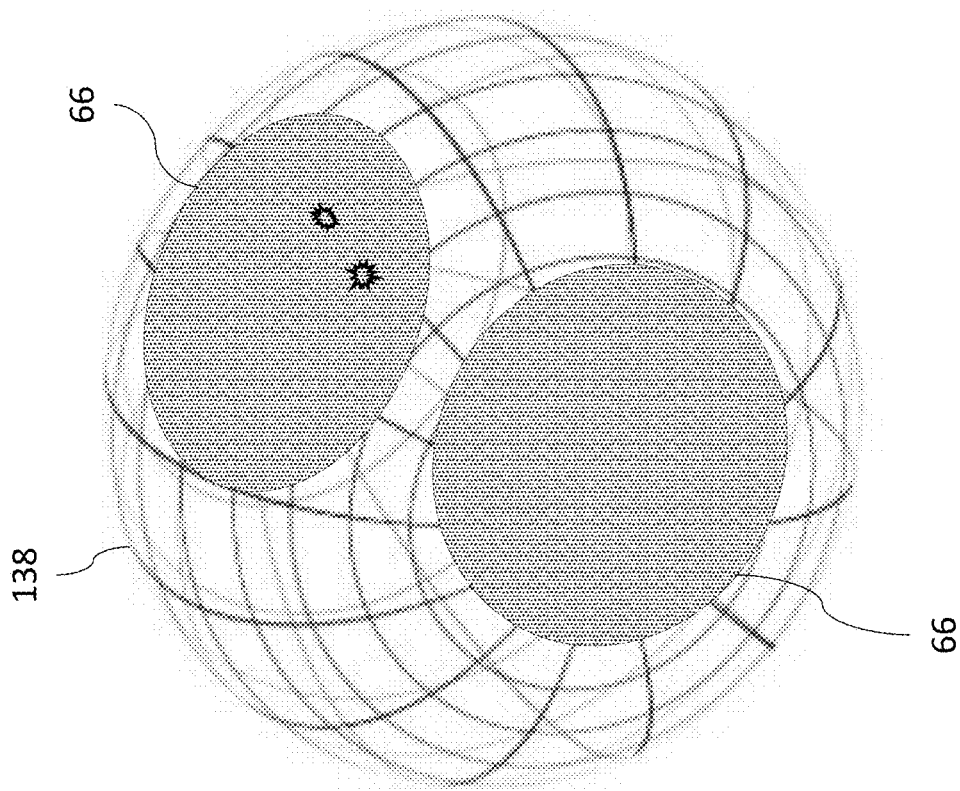
Figure 9C:
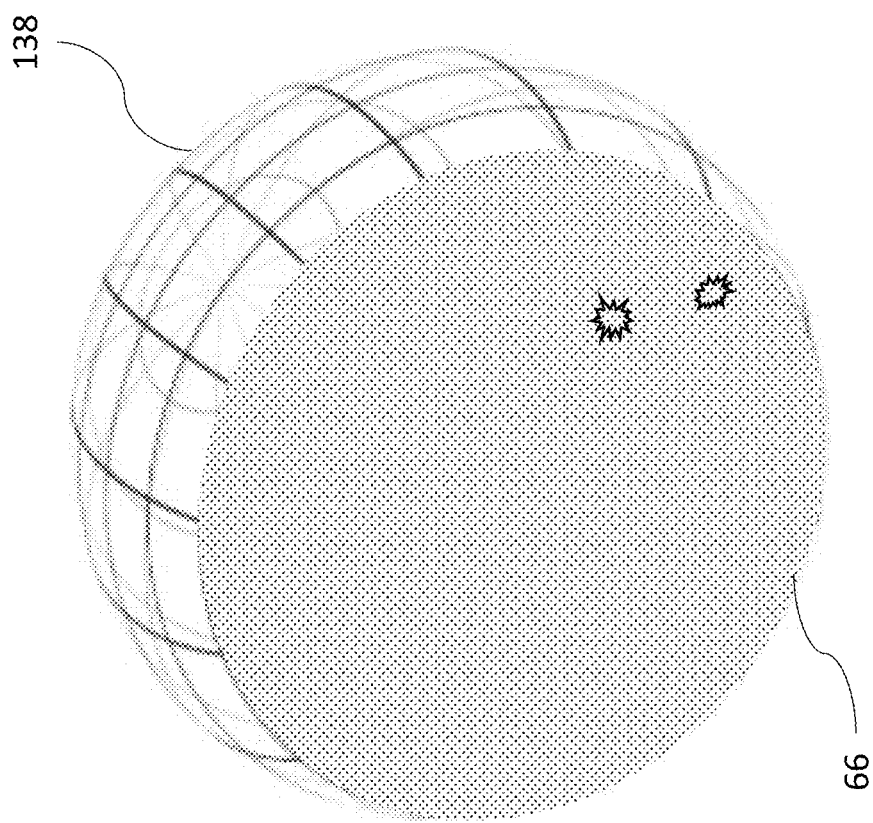

Reference is now made to FIGS. 9A-C, which are schematic views of a three-dimensional surface 138 for use in the apparatuses of FIGS. 1A and 1B. The three-dimensional surface 138 may be a sphere or any suitable three-dimensional shape. The images 66 captured by the camera 108 (FIGS. 6A-B) may be disposed on the surface according to the angle of deflection of the deflectable element 112 and the computed roll value of the distal end 104 when the respective images were captured by the camera 108. For example, an origin in a spherical coordinate system may be defined as a suitable point inside the three-dimensional surface 138, for example, at the center of the three-dimensional surface 138. The centers of the images 66 are then disposed on the three-dimensional surface 138 according to an azimuthal angle (e.g., the computed roll), and a polar angle (e.g., the angle of deflection) of each respective image 66. FIG. 9A shows two images 66 disposed on the three-dimensional surface 138. FIG. 9B shows the three-dimensional surface 138 rotated to a different orientation, for example, based on user input. FIG. 9C shows multiple images 66 disposed on the three-dimensional surface 138 providing a continual picture of about half of the vitreous humor 58 (FIG. 8E).

Reference is now made to FIGS. 10-12, which are flowcharts including steps in methods of operation of the apparatuses 10A, 10B of FIGS. 1A and 1B.

FIG. 10 shows a flowchart 140. The processor 20 (FIGS. 1A-B) is configured to compute (block 142) a deflection of the deflectable element 112 (FIGS. 6A-B). In some embodiments, the processor 20 is configured to compute the deflection of the deflectable element 112 responsively to an impedance of at least part of the puller wire 118 (FIGS. 6A-B). The processor 20 is configured to render (block 144) to the display 26 (FIGS. 1A-B) an indication of the computed deflection. The steps of blocks 142 and 144 are repeated intermittently.

FIG. 11 shows a flowchart 146. The camera 108 (FIGS. 6A-B) is configured to capture (block 148) an image. The processor 20 (FIGS. 1A-B) is configured to label (block 150) the captured image with the current computed roll value and current computed deflection of the deflectable element 112 (FIGS. 6A-B). The steps of blocks 148 and 150 are repeated for multiple images captured at different rolls and deflections of the probe 100 (FIGS. 6A-B). The processor 20 is configured to render (block 152) to the display 26 (FIGS. 1A-B) the respective images captured by the camera 108 of the respective inside portions of the eye on the three-dimensional surface 138 (FIG. 9A-C) responsively to the respective computed deflections and the computed roll values of the respective images as labeled in the step of block 150.

FIG. 12 shows a flowchart 154. The processor 20 (FIGS. 1A-B) is configured to receive (block 156) a user interface command to rotate the three-dimensional surface 138 (FIGS. 9A-C). The processor 20 is configured to render (block 158) to the display 26 (FIGS. 1A-B) a rotated view of the three-dimensional surface 138 responsively to the received user interface command. The steps of blocks 156 and 158 may be repeated when a new user interface command is received.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The exemplary embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. An eye examination apparatus to inspect a vitreous humor of an eye, comprising:
    a probe; wherein the probe, includes:
        a shaft including a distal end;
        a camera disposed at the distal end, wherein the distal end and the camera are configured to be inserted into the vitreous humor; and
        a magnetic orientation sensor disposed at a section of the shaft, wherein signals generated by the magnetic orientation sensor are used at least to compute roll values of the shaft;
    a display; and
    a processing circuitry;
        wherein the processing circuitry is configured to:
            receive respective signals from the magnetic orientation sensor while the shaft is twisted to respective orientations;
            compute respective roll values of the shaft at the respective orientations responsively to the respective received signals;
            output a notification responsively to at least one of the computed roll values; and
            render to the display respective images captured by the camera of respective inside portions of the eye.

2. The apparatus according to claim 1, wherein the camera fits into a space of about a 1 mm cube or less.

3. The apparatus according to claim 1, wherein the magnetic orientation sensor includes a magnetometer.

4. The apparatus according to claim 1, wherein the probe includes a phacoemulsification probe including a needle at the distal end, the camera facing away from the shaft.

5. The apparatus according to claim 4, further comprising a pump connected to the needle and configured to aspirate a cataract fragment from the vitreous humor.

6. The apparatus according to claim 1, wherein the distal end of the shaft includes a distal tip, the camera being disposed within 5 mm of the distal tip.

7. The apparatus according to claim 1, wherein the distal end of the shaft includes a deflectable element having a distal tip at which the camera is disposed, the magnetic orientation sensor being disposed in the shaft proximally to the deflectable element.

8. The apparatus according to claim 7, wherein the distal end of the shaft has an outside diameter of less than 2 mm.

9. The apparatus according to claim 7, wherein the deflectable element has a length of less than 5 mm and is configured to deflect by at least 120 degrees from an axis of a section of the shaft proximal to the deflectable element.

10. The apparatus according to claim 1, wherein the processing circuitry is further configured to:
    find when one of the computed roll values exceeds a predefined limit; and
    output a notification indicating that the one computed role value exceeds the predefined limit.

11. The apparatus according to claim 1, wherein the distal end of the shaft includes a deflectable element having a distal tip at which the camera is disposed, the magnetic orientation sensor being disposed in the shaft proximally to the deflectable element, the processing circuitry being configured to:
    compute a deflection of the deflectable element; and
    render to the display an indication of the computed deflection.

12. The apparatus according to claim 11, wherein the shaft includes a lumen and a puller wire having a proximal end and a distal end disposed in the lumen, the distal end of the puller wire being connected to the deflectable element so that pulling the proximal end of the puller wire in a proximal direction generates a deflection in the deflectable element, the processing circuitry being configured to compute the deflection of the deflectable element responsively to an impedance of at least part of the puller wire.

13. The apparatus according to claim 11, wherein the processing circuitry is configured to:
    render to the display the respective images captured by the camera of the respective inside portions of the eye on a three-dimensional surface responsively to the computed deflection and the computed roll values;
    receive a user interface command to rotate the three-dimensional surface; and
    render to the display a rotated view of the three-dimensional surface responsively to the received user interface command.

14. An eye examination method to inspect a vitreous humor of an eye, comprising:
    inserting a distal end of a shaft of a probe into the vitreous humor, the probe comprising a camera disposed at the distal end and a magnetic orientation sensor disposed at a section of the shaft, wherein signals generated by the magnetic orientation sensor are used at least to compute roll values of the shaft;
    receiving respective signals from the magnetic orientation sensor while the shaft is twisted to respective orientations;
    computing respective roll values of the shaft at the respective orientations responsively to the respective received signals;
    outputting a notification responsively to at least one of the computed roll values; and
    rendering to a display respective images captured by the camera of respective inside portions of the eye.

15. The method according to claim 14, further comprising aspirating a cataract fragment from the vitreous humor.

16. The method according to claim 14, further comprising performing a pars plana vitrectomy to remove a cataract fragment from the vitreous humor.

17. The method according to claim 14, further comprising:
    finding when one of the computed roll values exceeds a predefined limit; and
    outputting a notification indicating that the one computed role value exceeds the predefined limit.

18. The method according to claim 14, further comprising:
    computing a deflection of a deflectable element of the shaft, the camera being disposed at a distal tip of the deflectable element, the magnetic orientation sensor being disposed in the shaft proximally to the deflectable element; and
    rendering to the display an indication of the computed deflection.

19. The method according to claim 18, wherein computing the deflection includes computing the deflection of the deflectable element responsively to an impedance of at least part of a puller wire disposed in a lumen of the shaft and connected to the deflectable element so that pulling a proximal end of the puller wire in a proximal direction generates a deflection in the deflectable element.

20. The method according to claim 18, wherein the rendering includes rendering to the display the respective images captured by the camera of the respective inside portions of the eye on a three-dimensional surface responsively to the computed deflection and the computed roll values, the method further comprising receiving a user interface command to rotate the three-dimensional surface and rendering to the display a rotated view of the three-dimensional surface responsively to the received user interface command.

* * * * *